United States Patent
Alden et al.

(10) Patent No.: US 7,699,791 B2
(45) Date of Patent: *Apr. 20, 2010

(54) METHOD AND APPARATUS FOR IMPROVING SUCCESS RATE OF BLOOD YIELD FROM A FINGERSTICK

(75) Inventors: Don Alden, Sunnyvale, CA (US); Dominique M. Freeman, La Honda, CA (US); Paul Lum, Los Altos, CA (US); Vladimir Drbal, Belmont, CA (US); Dirk Boecker, Palo Alto, CA (US); Edward D. Verdonk, San Jose, CA (US)

(73) Assignee: Pelikan Technologies, Inc., Palo Alto, CA (US)

( * ) Notice: Subject to any disclaimer, the term of this patent is extended or adjusted under 35 U.S.C. 154(b) by 938 days.

This patent is subject to a terminal disclaimer.

(21) Appl. No.: 10/363,509

(22) PCT Filed: Jun. 12, 2002

(86) PCT No.: PCT/US02/19450

§ 371 (c)(1),
(2), (4) Date: Aug. 25, 2003

(87) PCT Pub. No.: WO02/100252

PCT Pub. Date: Dec. 19, 2002

(65) Prior Publication Data

US 2005/0101980 A1    May 12, 2005

(51) Int. Cl.
*A61B 5/00* (2006.01)

(52) U.S. Cl. .................................. 600/583; 606/181

(58) Field of Classification Search ................. 606/167, 606/172, 181, 182, 183; 600/573, 576, 577–579, 600/583
See application file for complete search history.

(56) References Cited

U.S. PATENT DOCUMENTS

| 2,714,890 A | 8/1955 | Vang ......................... 128/305 |
| 2,801,633 A | 8/1957 | Mauze et al. |
| 3,086,288 A | 4/1963 | Balamuth et al. ............. 30/272 |
| 3,208,452 A | 9/1965 | Stern ......................... 128/315 |

(Continued)

FOREIGN PATENT DOCUMENTS

DE        4420232        12/1995

(Continued)

OTHER PUBLICATIONS

International Search Report for International Application No. PCT/US02/19450.

(Continued)

*Primary Examiner*—Michael J Milano
*Assistant Examiner*—Victor X Nguyen
(74) *Attorney, Agent, or Firm*—Paul Davis; Goodwin Procter LLP

(57) ABSTRACT

Blood samples can be collected without substantial contamination from ambient air, such that the blood sample may be analyzed accurately for gaseous components such as oxygen and carbon dioxide. An embodiment of the device has integrated actuation, lancing, and sample acquisition components, which in some embodiments are miniatuized and/or disposable.

6 Claims, 5 Drawing Sheets

U.S. PATENT DOCUMENTS

| | | | | |
|---|---|---|---|---|
| 3,358,689 A | 12/1967 | Higgins | | 128/329 |
| 3,494,358 A | 2/1970 | Grossenbacker | | 128/218 |
| 3,626,929 A | 12/1971 | Sanz | | 128/2 R |
| 3,673,475 A | 6/1972 | Britton, Jr. | | 318/122 |
| 3,742,954 A | 7/1973 | Strickland | | 128/302 |
| 3,832,776 A | 9/1974 | Sawyer | | 30/272 |
| 3,953,172 A | 4/1976 | Shapiro | | 23/230 |
| 4,077,406 A | 3/1978 | Sandhage et al. | | 128/217 |
| 4,154,228 A | 5/1979 | Feldstein et al. | | 128/329 |
| 4,203,446 A | 5/1980 | Höfert et al. | | 128/329 |
| 4,223,674 A | 9/1980 | Fluent et al. | | 128/217 |
| 4,224,125 A | 9/1980 | Nakamura | | 204/195 B |
| 4,230,118 A | 10/1980 | Holman et al. | | 128/314 |
| 4,338,174 A | 7/1982 | Tamura | | 204/195 |
| 4,340,669 A | 7/1982 | Bauer | | 435/14 |
| 4,353,984 A | 10/1982 | Yamada | | 435/14 |
| 4,356,826 A | 11/1982 | Kubota | | 128/630 |
| 4,360,016 A | 11/1982 | Sarrine | | 128/763 |
| 4,391,905 A | 7/1983 | Bauer | | 435/14 |
| 4,391,906 A | 7/1983 | Bauer | | 435/14 |
| 4,414,975 A | 11/1983 | Ryder | | 128/314 |
| 4,420,564 A | 12/1983 | Tsuji | | 435/288 |
| 4,426,451 A | 1/1984 | Columbus | | 436/518 |
| 4,426,884 A | 1/1984 | Polchaninoff | | 73/172 |
| 4,449,529 A | 5/1984 | Burns et al. | | 128/314 |
| 4,462,405 A | 7/1984 | Ehrlich | | 128/329 |
| 4,469,110 A | 9/1984 | Slama | | 128/770 |
| 4,517,978 A | 5/1985 | Levin | | 128/314 |
| 4,518,384 A | 5/1985 | Tarello et al. | | 604/61 |
| 4,535,773 A | 8/1985 | Yoon | | 604/51 |
| 4,539,988 A | 9/1985 | Shirley | | 128/314 |
| 4,545,382 A | 10/1985 | Higgins | | 128/635 |
| 4,553,541 A | 11/1985 | Burns et al. | | 128/314 |
| 4,577,630 A | 3/1986 | Nitzsche | | 128/314 |
| 4,580,564 A | 4/1986 | Anderson | | 502/8 |
| 4,580,565 A | 4/1986 | Cornell | | 128/314 |
| 4,590,411 A | 5/1986 | Kelly | | 318/687 |
| 4,595,479 A | 6/1986 | Kimura | | 204/294 |
| 4,608,997 A | 9/1986 | Conway | | 128/763 |
| 4,615,340 A | 10/1986 | Cronenberg | | 128/635 |
| 4,616,649 A | 10/1986 | Burns | | 128/314 |
| 4,619,754 A | 10/1986 | Niki | | 204/290 |
| 4,622,974 A | 11/1986 | Coleman | | 128/634 |
| 4,624,253 A | 11/1986 | Burns | | 128/314 |
| 4,627,445 A | 12/1986 | Garcia et al. | | 128/770 |
| 4,637,393 A | 1/1987 | Ray | | 128/305 |
| 4,637,403 A | 1/1987 | Garcia et al. | | 128/770 |
| 4,643,189 A | 2/1987 | Mintz | | 128/314 |
| 4,648,408 A | 3/1987 | Hutcheson | | 128/770 |
| 4,653,511 A | 3/1987 | Goch | | 128/763 |
| 4,653,513 A | 3/1987 | Dombrowski | | 128/765 |
| 4,676,244 A | 6/1987 | Enstrom | | 128/314 |
| 4,677,979 A | 7/1987 | Burns | | 128/314 |
| 4,711,245 A | 12/1987 | Higgins | | 128/635 |
| 4,712,548 A | 12/1987 | Enstrom | | 128/314 |
| 4,715,374 A | 12/1987 | Maggio | | 128/314 |
| 4,735,203 A | 4/1988 | Ryder | | 128/314 |
| 4,750,489 A | 6/1988 | Berkman et al. | | 128/314 |
| 4,758,323 A | 7/1988 | Davis | | 204/403 |
| 4,787,398 A | 11/1988 | Garcia et al. | | 128/770 |
| 4,794,926 A | 1/1989 | Munsch et al. | | 128/314 |
| 4,814,142 A | 3/1989 | Gleisner | | 422/56 |
| 4,814,661 A | 3/1989 | Ratzlaff | | 310/328 |
| 4,820,010 A | 4/1989 | Sciefres | | 385/43 |
| 4,820,399 A | 4/1989 | Senda | | 204/403 |
| 4,823,806 A | 4/1989 | Bajada | | 128/744 |
| 4,824,639 A | 4/1989 | Hildenbrand | | 422/56 |
| RE32,922 E | 5/1989 | Levin et al. | | 128/314 |
| 4,827,763 A | 5/1989 | Bourland | | 73/172 |
| 4,830,959 A | 5/1989 | McNeill | | 435/53 |
| 4,836,904 A | 6/1989 | Armstron | | 204/294 |
| 4,844,095 A | 7/1989 | Chiodo | | 128/314 |
| 4,850,973 A | 7/1989 | Jordan | | 604/157 |
| 4,857,274 A | 8/1989 | Simon | | 422/72 |
| 4,869,249 A | 9/1989 | Crossman | | 128/314 |
| 4,869,265 A | 9/1989 | McEwen | | 128/774 |
| 4,873,993 A | 10/1989 | Meserol | | 128/780 |
| 4,882,013 A | 11/1989 | Turner | | 204/1 |
| 4,883,068 A | 11/1989 | Dechow | | 128/760 |
| 4,886,499 A | 12/1989 | Cirelli | | 604/131 |
| 4,889,529 A | 12/1989 | Haindl | | 604/274 |
| 4,892,097 A | 1/1990 | Ranalletta | | 606/182 |
| 4,895,147 A | 1/1990 | Bodicky | | 606/182 |
| 4,895,156 A | 1/1990 | Schulze | | 128/634 |
| 4,897,173 A | 1/1990 | Nankai | | 204/403 |
| 4,900,424 A | 2/1990 | Birch | | 204/409 |
| 4,911,794 A | 3/1990 | Parce | | 204/1 T |
| 4,920,977 A | 5/1990 | Haynes | | 128/770 |
| 4,924,879 A | 5/1990 | O'Brien | | 128/770 |
| 4,945,045 A | 7/1990 | Forrest | | 435/25 |
| 4,948,727 A | 8/1990 | Cass | | 435/18 |
| 4,952,515 A | 8/1990 | Gleisner | | 436/169 |
| 4,953,552 A | 9/1990 | DeMarzo | | 128/635 |
| 4,966,671 A | 10/1990 | Nylander | | 204/153.14 |
| 4,976,724 A | 12/1990 | Nieto | | 606/182 |
| 4,983,178 A | 1/1991 | Schnell | | 606/181 |
| 4,990,154 A | 2/1991 | Brown | | 606/182 |
| 4,995,402 A | 2/1991 | Smith et al. | | 128/771 |
| 4,999,582 A | 3/1991 | Parks | | 324/438 |
| 5,010,772 A | 4/1991 | Bourland | | 73/862.04 |
| 5,010,774 A | 4/1991 | Kikuo | | 73/862.04 |
| 5,014,718 A | 5/1991 | Mitchen | | 128/771 |
| 5,019,974 A | 5/1991 | Beckers | | 364/413.02 |
| 5,026,388 A | 6/1991 | Ingalz | | 606/182 |
| 5,029,583 A | 7/1991 | Meserol et al. | | 128/633 |
| 5,035,704 A | 7/1991 | Lambert et al. | | 606/182 |
| 5,047,044 A | 9/1991 | Smith et al. | | 606/182 |
| 5,054,499 A | 10/1991 | Swierczek | | 128/770 |
| 5,059,789 A | 10/1991 | Salcudean | | 250/206.1 |
| 5,060,174 A | 10/1991 | Gross | | 702/139 |
| 5,070,886 A | 12/1991 | Mitchen | | 128/771 |
| 5,074,872 A | 12/1991 | Brown | | 606/182 |
| 5,089,112 A | 2/1992 | Skotheim | | 204/403 |
| 5,092,842 A | 3/1992 | Bechtold | | 604/135 |
| 5,097,810 A | 3/1992 | Fishman et al. | | 128/743 |
| 5,100,427 A | 3/1992 | Crossman | | 606/182 |
| 5,100,428 A | 3/1992 | Mumford | | 606/182 |
| 5,104,380 A | 4/1992 | Holman | | 604/117 |
| 5,104,619 A | 4/1992 | Castro | | 422/56 |
| 5,108,564 A | 4/1992 | Szuminsky | | 204/153.12 |
| 5,116,759 A | 5/1992 | Klainer | | 435/288 |
| 5,120,420 A | 6/1992 | Nankai | | 204/403 |
| 5,122,244 A | 6/1992 | Hoenes | | 204/153 |
| 5,126,034 A | 6/1992 | Carter et al. | | 204/403 |
| 5,128,015 A | 7/1992 | Szuminsky | | 204/403 |
| 5,128,171 A | 7/1992 | Gleisner | | 427/2 |
| 5,133,730 A | 7/1992 | Biro | | 606/182 |
| 5,139,685 A | 8/1992 | Castro | | 210/767 |
| 5,141,868 A | 8/1992 | Shanks | | 435/288 |
| 5,145,565 A | 9/1992 | Kater et al. | | 204/153.1 |
| 5,152,775 A | 10/1992 | Ruppert | | 606/182 |
| 5,156,611 A | 10/1992 | Haynes | | 606/181 |
| 5,163,442 A | 11/1992 | Ono | | 128/760 |
| 5,170,364 A | 12/1992 | Gross | | 702/139 |
| D332,490 S | 1/1993 | Brown | | D24/146 |
| 5,178,142 A | 1/1993 | Harjunmaa | | 128/633 |
| 5,181,910 A | 1/1993 | Scanlon | | 604/67 |
| 5,181,914 A | 1/1993 | Zook | | 604/307 |
| 5,183,042 A | 2/1993 | Harjunmaa | | 128/633 |
| 5,185,256 A | 2/1993 | Nankai | | 435/174 |
| 5,187,100 A | 2/1993 | Matzinger | | 436/16 |
| 5,188,118 A | 2/1993 | Terwilliger | | 128/753 |
| 5,189,751 A | 3/1993 | Giuliani et al. | | 15/22.1 |
| 5,192,415 A | 3/1993 | Yoshioka | | 204/403 |

| Patent No. | Date | Inventor | Class |
|---|---|---|---|
| 5,196,025 A | 3/1993 | Ranalletta | 606/182 |
| 5,201,324 A | 4/1993 | Swierczek | 128/770 |
| 5,205,920 A | 4/1993 | Oyama | 204/403 |
| 5,212,879 A | 5/1993 | Biro | 29/437 |
| 5,216,597 A | 6/1993 | Beckers | 364/413.02 |
| 5,217,480 A | 6/1993 | Haber | 606/182 |
| 5,222,504 A | 6/1993 | Solomon | 128/744 |
| 5,228,972 A | 7/1993 | Osaka | 204/415 |
| 5,229,282 A | 7/1993 | Yoshioka | 435/177 |
| 5,230,866 A | 7/1993 | Shartle | 422/103 |
| 5,231,993 A | 8/1993 | Haber et al. | 128/770 |
| 5,250,066 A | 10/1993 | Lambert | 606/181 |
| 5,251,126 A | 10/1993 | Kahn | 364/413.11 |
| 5,253,656 A | 10/1993 | Rincoe | 128/782 |
| 5,256,998 A | 10/1993 | Becker | 335/229 |
| 5,264,103 A | 11/1993 | Yoshioka | 204/403 |
| 5,264,105 A | 11/1993 | Gregg | 204/403 |
| 5,264,106 A | 11/1993 | McAleer | 204/403 |
| 5,266,179 A | 11/1993 | Nankai | 204/401 |
| D342,673 S | 12/1993 | Cerola | D24/147 |
| 5,272,087 A | 12/1993 | El Murr | 435/291 |
| 5,277,181 A | 1/1994 | Mendelson | 128/633 |
| 5,279,294 A | 1/1994 | Anderson et al. | 128/633 |
| 5,282,822 A | 2/1994 | Macors | 606/182 |
| 5,286,362 A | 2/1994 | Hoenes | 204/403 |
| 5,286,364 A | 2/1994 | Yacynych | 204/418 |
| 5,288,636 A | 2/1994 | Pollman | 435/288 |
| 5,304,192 A | 4/1994 | Crouse | 606/181 |
| 5,304,193 A | 4/1994 | Zhadanov | 606/182 |
| 5,312,590 A | 5/1994 | Gunasingham | 422/56 |
| 5,314,441 A | 5/1994 | Cusack | 606/182 |
| 5,314,442 A | 5/1994 | Susumu | 606/182 |
| 5,316,012 A | 5/1994 | Siegal | 128/744 |
| 5,318,583 A | 6/1994 | Rabenau et al. | 606/182 |
| 5,320,607 A | 6/1994 | Ishibashi | 604/115 |
| 5,320,808 A | 6/1994 | Holen et al. | 422/64 |
| 5,324,302 A | 6/1994 | Crouse | 606/181 |
| 5,324,303 A | 6/1994 | Strong | 606/181 |
| 5,332,479 A | 7/1994 | Uenoyama | 204/153.12 |
| 5,350,392 A | 9/1994 | Purcell | 606/182 |
| 5,352,351 A | 10/1994 | White | 204/406 |
| 5,354,287 A | 10/1994 | Wacks | 604/232 |
| 5,354,447 A | 10/1994 | Uenoyama | 204/403 |
| 5,356,420 A | 10/1994 | Czernecki | 606/182 |
| 5,360,410 A | 11/1994 | Wacks | 604/232 |
| 5,366,469 A | 11/1994 | Steg | 606/182 |
| 5,366,470 A | 11/1994 | Ramel | 606/183 |
| 5,366,609 A | 11/1994 | White | 204/403 |
| 5,368,047 A | 11/1994 | Suzuki et al. | 128/765 |
| 5,371,687 A | 12/1994 | Holmes | 364/514 |
| 5,375,397 A | 12/1994 | Ferrand | 54/66 |
| 5,378,628 A | 1/1995 | Graetzel | 435/288 |
| 5,382,346 A | 1/1995 | Uenoyama | 204/403 |
| 5,383,885 A | 1/1995 | Bland | 606/182 |
| 5,389,534 A | 2/1995 | Gentezkow | 435/180 |
| 5,393,903 A | 2/1995 | Graetzel | 556/137 |
| 5,395,387 A | 3/1995 | Burns | 606/181 |
| 5,397,334 A | 3/1995 | Schenk | 606/182 |
| 5,401,376 A | 3/1995 | Foos | 204/415 |
| 5,402,798 A | 4/1995 | Swierczek | 128/770 |
| 5,405,511 A | 4/1995 | White | 204/153.1 |
| 5,407,545 A | 4/1995 | Hirose | 204/153.12 |
| 5,407,554 A | 4/1995 | Saurer | 204/403 |
| 5,407,818 A | 4/1995 | Gentezkow | 435/180 |
| 5,409,583 A | 4/1995 | Yoshioka | 204/153.12 |
| 5,410,059 A | 4/1995 | Fraser | 546/10 |
| 5,415,169 A | 5/1995 | Siczek et al. | 128/653.1 |
| 5,423,847 A | 6/1995 | Strong et al. | 606/182 |
| 5,436,161 A | 7/1995 | Bergstrom | 435/291 |
| 5,437,999 A | 8/1995 | Diebold | 435/288 |
| 5,438,271 A | 8/1995 | White | 324/444 |
| 5,443,701 A | 8/1995 | Willner | 204/153 |
| 5,445,920 A | 8/1995 | Saito | 430/311 |
| D362,719 S | 9/1995 | Kaplan | D24/147 |
| 5,454,828 A | 10/1995 | Schraga | 606/181 |
| 5,456,875 A | 10/1995 | Lambert | 264/328.1 |
| 5,464,418 A | 11/1995 | Schraga | 606/182 |
| 5,471,102 A | 11/1995 | Becker | 310/50 |
| 5,472,427 A | 12/1995 | Rammler | 604/164 |
| 5,474,084 A | 12/1995 | Cunniff | 128/744 |
| 5,476,474 A | 12/1995 | Davis | 606/182 |
| 5,480,387 A | 1/1996 | Gabriel | 604/134 |
| 5,487,748 A | 1/1996 | Marshall | 606/182 |
| 5,496,453 A | 3/1996 | Uenoyama | 205/777.5 |
| 5,498,542 A | 3/1996 | Corey | 435/283.1 |
| 5,507,288 A | 4/1996 | Bocker | 128/633 |
| 5,508,171 A | 4/1996 | Walling | 205/777.5 |
| 5,509,410 A | 4/1996 | Hill | 128/637 |
| 5,510,266 A | 4/1996 | Bonner et al. | 436/43 |
| 5,512,159 A | 4/1996 | Yoshioka | 204/403 |
| 5,514,152 A | 5/1996 | Smith | 606/182 |
| 5,518,006 A | 5/1996 | Mawhirt | 128/770 |
| 5,524,636 A | 6/1996 | Sarvazyan | 128/774 |
| 5,525,511 A | 6/1996 | D'Costa | 435/287.9 |
| 5,527,333 A | 6/1996 | Nikkels | 606/182 |
| 5,527,334 A | 6/1996 | Kanner | 606/182 |
| 5,529,074 A | 6/1996 | Greenfield | 128/744 |
| 5,540,709 A | 7/1996 | Ramel | 606/183 |
| 5,543,326 A | 8/1996 | Heller et al. | 435/287.9 |
| 5,545,174 A | 8/1996 | Schenk | 606/182 |
| 5,547,702 A | 8/1996 | Gleisner | 427/2.13 |
| 5,554,166 A | 9/1996 | Lange | 606/182 |
| 5,558,834 A | 9/1996 | Chu | 422/55 |
| 5,569,286 A | 10/1996 | Peckham | 606/181 |
| 5,569,287 A | 10/1996 | Tezuka | 606/182 |
| 5,571,132 A | 11/1996 | Mawhirt | 606/182 |
| 5,575,403 A | 11/1996 | Charlton et al. | 221/31 |
| 5,575,895 A | 11/1996 | Ikeda | 204/403 |
| 5,582,697 A | 12/1996 | Ikeda | 204/403 |
| 5,584,846 A | 12/1996 | Mawhirt | 606/182 |
| 5,593,852 A | 1/1997 | Heller | 435/14 |
| 5,609,749 A | 3/1997 | Yamauchi | 205/777.5 |
| 5,613,978 A | 3/1997 | Harding | 606/181 |
| 5,620,279 A | 4/1997 | Genshaw | 204/402 |
| 5,624,537 A | 4/1997 | Turner | 204/403 |
| D379,516 S | 5/1997 | Rutter | D24/146 |
| 5,628,764 A | 5/1997 | Schraga | 606/182 |
| 5,628,765 A | 5/1997 | Morita | 606/182 |
| 5,628,890 A | 5/1997 | Carter | 204/403 |
| 5,630,986 A | 5/1997 | Charlton et al. | 422/64 |
| 5,632,410 A | 5/1997 | Moulton et al. | 221/79 |
| 5,640,954 A | 6/1997 | Pfeiffer | 128/635 |
| 5,643,306 A | 7/1997 | Schraga | 606/182 |
| 5,645,555 A | 7/1997 | Davis | 606/182 |
| 5,650,062 A | 7/1997 | Ikeda | 205/778 |
| 5,653,863 A | 8/1997 | Genshaw | 205/777.5 |
| 5,657,760 A | 8/1997 | Ying et al. | 128/660.03 |
| 5,658,444 A | 8/1997 | Black | 204/415 |
| 5,662,127 A | 9/1997 | De Vaughn | 128/765 |
| 5,662,672 A | 9/1997 | Pambianchi | 606/181 |
| 5,676,143 A | 10/1997 | Simonsen | 128/633 |
| 5,680,858 A | 10/1997 | Hansen et al. | 128/635 |
| 5,680,872 A | 10/1997 | Sesekura | 128/760 |
| 5,682,884 A | 11/1997 | Hill | 128/637 |
| 5,683,562 A | 11/1997 | Schaffar | 204/403 |
| 5,695,947 A | 12/1997 | Guo | 435/11 |
| 5,700,695 A | 12/1997 | Yassinzadeh et al. | 436/180 |
| 5,705,045 A | 1/1998 | Park | 204/403 |
| 5,708,247 A | 1/1998 | McAleer | 204/403 |
| 5,709,668 A | 1/1998 | Wacks | 604/232 |
| 5,709,699 A | 1/1998 | Warner | 606/181 |
| 5,710,011 A | 1/1998 | Forrow | 435/25 |
| 5,714,390 A | 2/1998 | Hallowitz et al. | 436/526 |
| 5,720,862 A | 2/1998 | Hamamoto | 204/403 |
| 5,720,924 A | 2/1998 | Eikmeier et al. | 422/102 |
| D392,391 S | 3/1998 | Douglas | D24/225 |

| Patent No. | Date | Inventor | Class |
|---|---|---|---|
| 5,723,284 A | 3/1998 | Ye | 435/4 |
| 5,727,548 A | 3/1998 | Hill | 128/637 |
| 5,730,753 A | 3/1998 | Susumu | 606/181 |
| 5,733,300 A | 3/1998 | Pambianchi | 606/181 |
| D393,716 S | 4/1998 | Brenneman | D24/147 |
| D393,717 S | 4/1998 | Brenneman | D24/147 |
| 5,738,244 A | 4/1998 | Charlton et al. | 221/26 |
| 5,741,228 A | 4/1998 | Lambrecht | 604/93 |
| 5,741,634 A | 4/1998 | Nozoe | 435/4 |
| RE35,803 E | 5/1998 | Lange | 606/182 |
| 5,746,217 A | 5/1998 | Erickson | 128/760 |
| 5,746,898 A | 5/1998 | Preidel | 204/403 |
| 5,755,733 A | 5/1998 | Susumu | 606/182 |
| 5,758,643 A | 6/1998 | Wong et al. | 128/632 |
| 5,759,364 A | 6/1998 | Charlton | 204/403 |
| 5,762,770 A | 6/1998 | Pritchard | 204/403 |
| 5,770,369 A | 6/1998 | Meade | 435/6 |
| 5,772,586 A | 6/1998 | Heinonen | 600/300 |
| 5,772,677 A | 6/1998 | Mawhirt | 606/181 |
| 5,773,270 A | 6/1998 | D'Orazio | 435/177 |
| 5,776,157 A | 7/1998 | Thorne et al. | 606/182 |
| 5,776,719 A | 7/1998 | Douglas | 435/28 |
| 5,779,365 A | 7/1998 | Takaki | 374/117 |
| 5,782,770 A | 7/1998 | Mooradian | 600/476 |
| 5,782,852 A | 7/1998 | Foggia | 606/182 |
| 5,788,651 A | 8/1998 | Weilandt | 600/567 |
| 5,788,652 A | 8/1998 | Rahn | 600/577 |
| 5,794,219 A | 8/1998 | Brown | 705/37 |
| 5,795,725 A | 8/1998 | Buechler | 435/7.1 |
| 5,795,774 A | 8/1998 | Matsumoto | 435/287.9 |
| 5,797,940 A | 8/1998 | Mawhirt | 606/167 |
| 5,797,942 A | 8/1998 | Schraga | 606/182 |
| 5,798,030 A | 8/1998 | Raguse | 204/403 |
| 5,798,031 A | 8/1998 | Charlton | 204/403 |
| 5,800,781 A | 9/1998 | Gavin et al. | 422/73 |
| 5,801,057 A | 9/1998 | Smart et al. | 436/68 |
| 5,807,375 A | 9/1998 | Gross | 604/890.1 |
| 5,810,199 A | 9/1998 | Charlton et al. | 221/31 |
| 5,820,551 A | 10/1998 | Hill | 600/347 |
| 5,822,715 A | 10/1998 | Worthington | 702/19 |
| 5,823,973 A | 10/1998 | Racchini et al. | 600/573 |
| 5,824,491 A | 10/1998 | Priest | 435/28 |
| 5,828,943 A | 10/1998 | Brown | 434/258 |
| 5,830,219 A | 11/1998 | Bird et al. | 606/130 |
| 5,832,448 A | 11/1998 | Brown | 705/2 |
| 5,840,020 A | 11/1998 | Heinonen | 600/309 |
| 5,840,171 A | 11/1998 | Birch | 205/335 |
| 5,846,490 A | 12/1998 | Yokota et al. | 422/66 |
| 5,849,174 A | 12/1998 | Sanghera | 205/775 |
| 5,853,373 A | 12/1998 | Griffith | 600/554 |
| 5,854,074 A | 12/1998 | Charlton et al. | 436/46 |
| D403,975 S | 1/1999 | Douglas | D10/81 |
| 5,855,801 A | 1/1999 | Lin et al. | 216/2 |
| 5,857,983 A | 1/1999 | Douglas | 600/538 |
| 5,860,922 A | 1/1999 | Gordon et al. | 600/431 |
| 5,863,800 A | 1/1999 | Eikmeier et al. | 436/48 |
| 5,866,353 A | 2/1999 | Berneth | 435/26 |
| 5,868,135 A | 2/1999 | Kaufman | 128/630 |
| 5,868,772 A | 2/1999 | LeVaughn | 606/181 |
| 5,869,972 A | 2/1999 | Birch | 324/439 |
| 5,871,494 A | 2/1999 | Simons et al. | 606/181 |
| 5,872,713 A | 2/1999 | Douglas | 702/85 |
| 5,873,887 A | 2/1999 | King | 606/182 |
| 5,876,957 A | 3/1999 | Douglas | 435/28 |
| 5,879,163 A | 3/1999 | Brown | 434/236 |
| 5,879,310 A | 3/1999 | Sopp | 600/578 |
| 5,879,311 A | 3/1999 | Duchon et al. | 600/583 |
| 5,879,373 A | 3/1999 | Roeper | 606/344 |
| 5,880,829 A | 3/1999 | Kauhaniemi et al. | 356/246 |
| 5,882,494 A | 3/1999 | van Antwerp | 204/403 |
| 5,885,211 A | 3/1999 | Eppstein et al. | 600/309 |
| 5,887,133 A | 3/1999 | Brown | 395/200.3 |
| RE36,191 E | 4/1999 | Solomon | 395/308 |
| 5,891,053 A | 4/1999 | Sesekura | 600/583 |
| 5,893,870 A | 4/1999 | Talen | 606/201 |
| 5,897,493 A | 4/1999 | Brown | 600/300 |
| 5,899,855 A | 5/1999 | Brown | 600/301 |
| 5,899,915 A | 5/1999 | Saadat et al. | |
| 5,900,130 A | 5/1999 | Benvegnu | 204/453 |
| 5,906,921 A | 5/1999 | Ikeda | 435/25 |
| D411,619 S | 6/1999 | Duchon | D24/146 |
| 5,913,310 A | 6/1999 | Brown | 128/897 |
| 5,916,156 A | 6/1999 | Hildenbrand | 600/347 |
| 5,916,229 A | 6/1999 | Evans | 606/171 |
| 5,916,230 A | 6/1999 | Brenneman | 606/172 |
| 5,918,603 A | 7/1999 | Brown | 128/897 |
| 5,921,963 A | 7/1999 | Erez | 604/192 |
| 5,922,188 A | 7/1999 | Ikeda | 204/777.5 |
| RE36,268 E | 8/1999 | Szuminsky | 205/777.5 |
| 5,933,136 A | 8/1999 | Brown | 345/327 |
| 5,935,075 A | 8/1999 | Casscells et al. | 600/474 |
| 5,938,679 A | 8/1999 | Freeman et al. | 606/181 |
| 5,942,102 A | 8/1999 | Hodges | 205/775 |
| 5,951,300 A | 9/1999 | Brown | 434/236 |
| 5,951,492 A | 9/1999 | Douglas | 600/583 |
| 5,951,493 A | 9/1999 | Douglas et al. | 600/583 |
| 5,951,582 A | 9/1999 | Thorne et al. | 606/182 |
| 5,951,836 A | 9/1999 | McAleer | 204/403 |
| 5,954,738 A | 9/1999 | LeVaughn | 606/181 |
| 5,956,501 A | 9/1999 | Brown | 395/500.32 |
| 5,958,199 A | 9/1999 | Miyamoto | 204/403 |
| 5,960,403 A | 9/1999 | Brown | 705/2 |
| 5,964,718 A | 10/1999 | Duchon | 600/583 |
| 5,965,380 A | 10/1999 | Heller | 435/14 |
| 5,968,063 A | 10/1999 | Chu et al. | 606/185 |
| 5,971,941 A | 10/1999 | Simons et al. | 600/573 |
| 5,972,199 A | 10/1999 | Heller | 205/777.5 |
| 5,972,715 A | 10/1999 | Celentano | 436/164 |
| 5,974,124 A | 10/1999 | Schlueter | 379/106.02 |
| 5,983,193 A | 11/1999 | Heinonen | 705/2 |
| 5,985,116 A | 11/1999 | Ikeda | 204/403 |
| 5,985,559 A | 11/1999 | Brown | 435/6 |
| 5,993,400 A | 11/1999 | Rincoe | 600/595 |
| 5,997,476 A | 12/1999 | Brown | 600/300 |
| 5,997,561 A | 12/1999 | Böcker et al. | 606/182 |
| 5,997,817 A | 12/1999 | Crismore | 422/58 |
| 5,997,818 A | 12/1999 | Hackner | 422/81 |
| 6,001,067 A | 12/1999 | Shults | 600/584 |
| 6,015,392 A | 1/2000 | Douglas | 600/583 |
| 6,020,110 A | 2/2000 | Williams | 430/315 |
| 6,022,324 A | 2/2000 | Skinner | 600/566 |
| 6,022,366 A | 2/2000 | Schraga | 606/181 |
| 6,023,686 A | 2/2000 | Brown | 705/37 |
| 6,027,459 A | 2/2000 | Shain et al. | 600/573 |
| 6,030,399 A | 2/2000 | Ignotz | 606/167 |
| 6,030,827 A | 2/2000 | Davis | 435/287 |
| 6,032,119 A | 2/2000 | Brown | 705/2 |
| 6,033,421 A | 3/2000 | Theiss | 606/186 |
| 6,033,866 A | 3/2000 | Guo | 435/14 |
| 6,036,924 A | 3/2000 | Simons et al. | 422/100 |
| 6,041,253 A | 3/2000 | Kost | 604/20 |
| 6,048,352 A | 4/2000 | Douglas et al. | 606/181 |
| D424,696 S | 5/2000 | Ray | D24/169 |
| 6,056,701 A | 5/2000 | Duchon | 600/583 |
| 6,060,327 A | 5/2000 | Keen | 436/518 |
| 6,061,128 A | 5/2000 | Zweig | 356/243.4 |
| 6,063,039 A | 5/2000 | Cunningham | 600/573 |
| 6,066,103 A | 5/2000 | Duchon | 600/583 |
| 6,066,296 A | 5/2000 | Brady | 422/63 |
| 6,067,463 A | 5/2000 | Jeng | 600/336 |
| 6,068,615 A | 5/2000 | Brown | 604/207 |
| D426,638 S | 6/2000 | Ray | D24/169 |
| 6,071,249 A | 6/2000 | Cunningham | 600/578 |
| 6,071,250 A | 6/2000 | Douglas | 600/583 |
| 6,071,251 A | 6/2000 | Cunningham | 600/584 |
| 6,071,294 A | 6/2000 | Simons et al. | 606/181 |

| | | | | | | | |
|---|---|---|---|---|---|---|---|
| 6,074,360 | A | 6/2000 | Hans-Peter ............... 604/57 | 6,251,260 | B1 | 6/2001 | Heller ................. 205/777.5 |
| 6,077,408 | A | 6/2000 | Miyamoto ............... 204/403 | 6,254,831 | B1 | 7/2001 | Barnard ................ 422/82.08 |
| 6,080,172 | A | 6/2000 | Fujiwara ................. 606/166 | 6,256,533 | B1 | 7/2001 | Vuzhakov ................. 604/21 |
| 6,083,710 | A | 7/2000 | Heller ..................... 435/14 | 6,258,229 | B1 | 7/2001 | Winarta ................... 204/403 |
| 6,086,545 | A | 7/2000 | Roe ........................ 600/570 | 6,258,254 | B1 | 7/2001 | Miyamoto ............ 205/777.5 |
| 6,086,562 | A | 7/2000 | Jacobsen ................. 604/156 | 6,261,241 | B1 | 7/2001 | Burbank et al. ........... 600/564 |
| 6,090,078 | A | 7/2000 | Erskine ................... 604/198 | 6,261,245 | B1 | 7/2001 | Kawai et al. ............. 600/576 |
| 6,093,146 | A | 7/2000 | Filangeri ................. 600/300 | 6,261,519 | B1 | 7/2001 | Harding |
| 6,093,156 | A | 7/2000 | Cunningham et al. ....... 600/573 | 6,268,161 | B1 | 7/2001 | Han .......................... 435/14 |
| 6,101,478 | A | 8/2000 | Brown ....................... 705/2 | 6,270,455 | B1 | 8/2001 | Brown ................... 600/300 |
| 6,103,033 | A | 8/2000 | Say ........................ 156/73.1 | 6,270,637 | B1 | 8/2001 | Crismore ................ 204/403 |
| 6,107,083 | A | 8/2000 | Collins ..................... 435/288 | 6,272,359 | B1 | 8/2001 | Kivela ..................... 455/567 |
| 6,113,578 | A | 9/2000 | Brown ..................... 604/207 | 6,281,006 | B1 | 8/2001 | Heller ................... 435/287.9 |
| 6,117,630 | A | 9/2000 | Reber et al. .................. 435/4 | 6,283,926 | B1 | 9/2001 | Cunningham et al. ....... 600/573 |
| 6,120,462 | A | 9/2000 | Hibner et al. ............. 600/566 | 6,283,982 | B1 | 9/2001 | Levaughn ................ 606/172 |
| 6,120,676 | A | 9/2000 | Heller .................. 205/777.5 | 6,284,478 | B1 | 9/2001 | Heller ....................... 435/14 |
| 6,121,009 | A | 9/2000 | Heller ....................... 435/14 | 6,285,448 | B1 | 9/2001 | Kuenstner .................. 356/39 |
| 6,122,536 | A | 9/2000 | Sun ......................... 600/341 | 6,285,454 | B1 | 9/2001 | Douglas et al. ............ 356/446 |
| 6,129,823 | A | 10/2000 | Hughes ................ 204/403.01 | 6,290,683 | B1 | 9/2001 | Erez ....................... 604/273 |
| 6,132,449 | A | 10/2000 | Lum et al. ................. 606/181 | 6,294,897 | B1 | 9/2001 | Champlin ................ 320/153 |
| 6,133,837 | A | 10/2000 | Riley ...................... 340/573.1 | 6,295,506 | B1 | 9/2001 | Heinonen ................ 702/104 |
| 6,134,461 | A | 10/2000 | Say ......................... 600/345 | 6,299,757 | B1 | 10/2001 | Feldman ................. 205/775 |
| 6,136,013 | A | 10/2000 | Marshall et al. ............. 606/167 | 6,302,844 | B1 | 10/2001 | Walker ................... 600/300 |
| 6,139,562 | A | 10/2000 | Mauze et al. ............. 606/171 | 6,302,855 | B1 | 10/2001 | Lav ........................ 600/584 |
| 6,143,164 | A | 11/2000 | Heller et al. ............ 205/777.5 | 6,305,804 | B1 | 10/2001 | Rice ........................ 351/221 |
| 6,144,837 | A | 11/2000 | Quy ..................... 434/307 R | 6,306,104 | B1 | 10/2001 | Cunningham et al. ....... 600/573 |
| 6,151,586 | A | 11/2000 | Brown ....................... 705/14 | 6,306,152 | B1 | 10/2001 | Verdonk et al. ........... 606/182 |
| 6,152,875 | A | 11/2000 | Hakamata ................ 600/319 | 6,306,347 | B1 | 10/2001 | Mason ...................... 422/58 |
| 6,152,942 | A | 11/2000 | Brenneman et al. .......... 606/181 | 6,309,535 | B1 | 10/2001 | Williams ............... 205/777.5 |
| 6,153,069 | A | 11/2000 | Pottgen .................... 204/403 | 6,312,612 | B1 | 11/2001 | Sherman ................... 216/2 |
| RE36,991 | E | 12/2000 | Yamamoto ................ 204/403 | 6,315,738 | B1 | 11/2001 | Nishikawa et al. .......... 600/583 |
| 6,155,267 | A | 12/2000 | Nelson ..................... 128/899 | 6,319,210 | B1 | 11/2001 | Douglas et al. ............ 600/583 |
| 6,155,992 | A | 12/2000 | Henning et al. ............ 600/583 | 6,322,574 | B1 | 11/2001 | Lloyd ...................... 606/181 |
| 6,156,051 | A | 12/2000 | Schraga ................... 606/181 | 6,329,161 | B1 | 12/2001 | Heller ....................... 435/14 |
| 6,157,442 | A | 12/2000 | Raskas ...................... 356/39 | 6,330,426 | B2 | 12/2001 | Brown ................. 434/307 R |
| 6,159,424 | A | 12/2000 | Kauhaniemi et al. .......... 422/63 | 6,331,163 | B1 | 12/2001 | Kaplan ................... 600/486 |
| 6,161,095 | A | 12/2000 | Brown ....................... 705/2 | 6,332,871 | B1 | 12/2001 | Douglas et al. ............ 600/583 |
| 6,162,611 | A | 12/2000 | Heller ....................... 435/14 | 6,334,363 | B1 | 1/2002 | Testud ....................... 73/862 |
| 6,167,362 | A | 12/2000 | Brown ....................... 703/11 | 6,334,778 | B1 | 1/2002 | Brown .................... 434/258 |
| 6,167,386 | A | 12/2000 | Brown ....................... 705/37 | 6,334,856 | B1 | 1/2002 | Allen ....................... 604/191 |
| 6,168,563 | B1 | 1/2001 | Brown ..................... 600/301 | 6,338,790 | B1 | 1/2002 | Feldman ................. 205/777.5 |
| 6,171,325 | B1 | 1/2001 | Mauze et al. ............. 606/171 | 6,349,229 | B1 | 2/2002 | Watanabe ................ 600/345 |
| 6,175,752 | B1 | 1/2001 | Say ......................... 600/345 | 6,350,273 | B1 | 2/2002 | Minagawa ............... 606/186 |
| 6,176,865 | B1 | 1/2001 | Mauze et al. ............. 606/171 | 6,350,451 | B1 | 2/2002 | Horn ....................... 424/184.1 |
| 6,177,000 | B1 | 1/2001 | Peterson .................. 205/777.5 | 6,352,514 | B1 | 3/2002 | Douglas et al. ............ 600/583 |
| 6,177,931 | B1 | 1/2001 | Alexander et al. | 6,352,523 | B1 | 3/2002 | Brown .................... 604/207 |
| 6,183,489 | B1 | 2/2001 | Douglas et al. ............ 606/181 | 6,353,753 | B1 | 3/2002 | Flock ...................... 600/473 |
| 6,186,145 | B1 | 2/2001 | Brown ..................... 128/897 | 6,364,889 | B1 | 4/2002 | Kheiri et al. ............... 606/181 |
| 6,190,612 | B1 | 2/2001 | Berger .................... 422/82.07 | 6,364,890 | B1 | 4/2002 | Lum et al. ................. 606/181 |
| 6,191,852 | B1 | 2/2001 | Paffhausen ................ 356/244 | 6,368,273 | B1 | 4/2002 | Brown .................... 600/300 |
| 6,192,891 | B1 | 2/2001 | Gravel ...................... 128/920 | 6,375,469 | B1 | 4/2002 | Brown .................... 434/236 |
| 6,193,673 | B1 | 2/2001 | Viola et al. ................ 600/568 | 6,375,627 | B1 | 4/2002 | Mauze et al. ............. 600/584 |
| 6,194,900 | B1 | 2/2001 | Freeman .................. 324/321 | 6,379,301 | B1 | 4/2002 | Worthington ............. 600/309 |
| 6,197,257 | B1 | 3/2001 | Raskas ................... 422/82.05 | 6,379,317 | B1 | 4/2002 | Kintzig et al. ............. 600/573 |
| 6,203,504 | B1 | 3/2001 | Latterell et al. ............. 600/576 | 6,379,324 | B1 | 4/2002 | Gartstein .................... 604/22 |
| 6,206,841 | B1 | 3/2001 | Cunningham et al. ....... 600/584 | 6,379,969 | B1 | 4/2002 | Mauze et al. ................ 436/68 |
| 6,210,272 | B1 | 4/2001 | Brown ....................... 463/1 | 6,381,577 | B1 | 4/2002 | Brown ....................... 705/2 |
| 6,210,420 | B1 | 4/2001 | Mauze et al. ............. 606/181 | 6,387,709 | B1 | 5/2002 | Mason .................... 436/164 |
| 6,210,421 | B1 | 4/2001 | Böcker et al. ............. 606/182 | 6,391,005 | B1 | 5/2002 | Lum et al. ................. 604/117 |
| 6,212,417 | B1 | 4/2001 | Ikeda .................... 204/403.14 | 6,399,394 | B1 | 6/2002 | Dahm ..................... 436/180 |
| 6,214,804 | B1 | 4/2001 | Felgner ...................... 514/44 | 6,402,701 | B1 | 6/2002 | Kaplan et al. ............. 600/567 |
| 6,221,238 | B1 | 4/2001 | Grundig ................. 205/777.5 | 6,402,704 | B1 | 6/2002 | McMorrow ............... 600/576 |
| 6,225,078 | B1 | 5/2001 | Ikeda ......................... 435/25 | 6,409,740 | B1 | 6/2002 | Kuhr et al. ................ 606/182 |
| 6,228,100 | B1 | 5/2001 | Schraga ................... 606/183 | 6,413,410 | B1 | 7/2002 | Hodges ................... 205/775 |
| 6,230,501 | B1 | 5/2001 | Bailey ....................... 62/51.1 | 6,413,411 | B1 | 7/2002 | Pottgen .................. 205/777.5 |
| 6,231,531 | B1 | 5/2001 | Lum et al. ................. 601/46 | 6,421,633 | B1 | 7/2002 | Heinonen ................. 703/11 |
| 6,233,471 | B1 | 5/2001 | Berner ..................... 600/345 | 6,423,014 | B1 | 7/2002 | Churchill et al. |
| 6,233,539 | B1 | 5/2001 | Brown ....................... 703/11 | 6,428,664 | B1 | 8/2002 | Bhullar .................. 204/403.03 |
| 6,240,393 | B1 | 5/2001 | Brown ....................... 705/1 | 6,436,256 | B1 | 8/2002 | Williams ............... 204/403.06 |
| 6,241,862 | B1 | 6/2001 | McAleer ................... 204/403 | 6,436,721 | B1 | 8/2002 | Kuo ........................ 436/514 |
| 6,245,060 | B1 | 6/2001 | Loomis ....................... 606/9 | 6,440,645 | B1 | 8/2002 | Yon-Hin .................. 430/322 |
| 6,246,992 | B1 | 6/2001 | Brown ....................... 705/2 | 6,451,040 | B1 | 9/2002 | Purcell ..................... 606/181 |
| 6,248,065 | B1 | 6/2001 | Brown ..................... 600/300 | 6,458,258 | B2 | 10/2002 | Taniike ..................... 204/403 |

| Patent | Kind | Date | Name | Class |
|---|---|---|---|---|
| 6,461,496 | B1 | 10/2002 | Feldman et al. | 205/777.5 |
| 6,462,162 | B2 | 10/2002 | van Antwerp | 528/77 |
| 6,464,649 | B1 | 10/2002 | Duchon | 600/583 |
| 6,471,903 | B2 | 10/2002 | Sherman | 264/328.1 |
| 6,472,220 | B1 | 10/2002 | Simons et al. | 436/63 |
| 6,475,436 | B1 | 11/2002 | Schabbach | 422/64 |
| 6,475,750 | B1 | 11/2002 | Han | 435/14 |
| 6,477,394 | B2 | 11/2002 | Rice | 600/318 |
| 6,477,424 | B1 | 11/2002 | Thompson | 607/60 |
| 6,484,046 | B1 | 11/2002 | Say | 600/345 |
| 6,485,439 | B1 | 11/2002 | Roe et al. | 600/578 |
| 6,488,891 | B2 | 12/2002 | Mason et al. | 422/58 |
| 6,491,709 | B2 | 12/2002 | Sharma et al. | 606/181 |
| 6,494,830 | B1 | 12/2002 | Wessel | 600/300 |
| 6,497,845 | B1 | 12/2002 | Sacherer | 422/104 |
| 6,501,404 | B2 | 12/2002 | Walker | 341/143 |
| 6,503,210 | B1 | 1/2003 | Hirao et al. | 600/576 |
| 6,503,231 | B1 | 1/2003 | Praunsnitz | 604/272 |
| 6,503,381 | B1 | 1/2003 | Gotoh | 204/403.14 |
| 6,506,168 | B1 | 1/2003 | Fathallah | 600/578 |
| 6,506,575 | B1 | 1/2003 | Knappe et al. | 435/25 |
| 6,508,795 | B1 | 1/2003 | Eppstein | 604/113 |
| 6,514,270 | B1 | 2/2003 | Schraga | 606/182 |
| 6,514,460 | B1 | 2/2003 | Fendrock | 422/55 |
| 6,519,241 | B1 | 2/2003 | Theimer | 370/338 |
| 6,520,326 | B2 | 2/2003 | McIvor | 206/305 |
| 6,527,778 | B2 | 3/2003 | Athanasiou | 606/80 |
| 6,530,892 | B1 | 3/2003 | Kelly | 600/583 |
| 6,530,937 | B1 | 3/2003 | Schraga | 606/182 |
| 6,533,949 | B1 | 3/2003 | Yeshurun | 216/11 |
| 6,537,207 | B1 | 3/2003 | Rice | 600/121 |
| 6,537,242 | B1 | 3/2003 | Palmer | 604/22 |
| 6,537,292 | B1 | 3/2003 | Lee | 606/182 |
| 6,540,672 | B1 | 4/2003 | Simonsen | 600/300 |
| 6,540,675 | B2 | 4/2003 | Aceti | 600/309 |
| 6,540,762 | B1 | 4/2003 | Bertling | 606/182 |
| 6,540,891 | B1 | 4/2003 | Stewart | 204/403.4 |
| 6,541,266 | B2 | 4/2003 | Modzelewski | 436/95 |
| 6,547,954 | B2 | 4/2003 | Ikeda | 205/777.5 |
| 6,549,796 | B2 | 4/2003 | Sohrab | 600/345 |
| 6,551,494 | B1 | 4/2003 | Heller | 205/777.5 |
| 6,553,244 | B2 | 4/2003 | Lesho | 600/347 |
| 6,554,381 | B2 | 4/2003 | Locher | 347/7 |
| 6,555,061 | B1 | 4/2003 | Leong | 422/58 |
| 6,558,320 | B1 | 5/2003 | Causey | 600/300 |
| 6,558,361 | B1 | 5/2003 | Yeshurun | 604/272 |
| 6,558,402 | B1 | 5/2003 | Chelak | 606/182 |
| 6,558,528 | B1 | 5/2003 | Matzinger | 205/777.5 |
| 6,560,471 | B1 | 5/2003 | Heller | 600/347 |
| 6,561,978 | B1 | 5/2003 | Conn | 600/309 |
| 6,561,989 | B2 | 5/2003 | Whitson | 600/573 |
| 6,562,210 | B1 | 5/2003 | Bhullar | 204/403.3 |
| 6,565,509 | B1 | 5/2003 | Say et al. | 600/365 |
| 6,565,808 | B2 | 5/2003 | Hudak | 422/58 |
| 6,569,157 | B1 | 5/2003 | Shain | 606/12 |
| 6,571,651 | B1 | 6/2003 | Hodges | 73/864.72 |
| 6,572,566 | B2 | 6/2003 | Effenhauser | 600/584 |
| 6,574,490 | B2 | 6/2003 | Abbink | 600/316 |
| 6,575,905 | B2 | 6/2003 | Knobbe | 600/365 |
| 6,576,101 | B1 | 6/2003 | Heller | 204/403.14 |
| 6,576,117 | B1 | 6/2003 | Iketaki et al. | 205/777.5 |
| 6,576,416 | B2 | 6/2003 | Haviland | 435/4 |
| 6,582,573 | B2 | 6/2003 | Douglas | 204/403.1 |
| 6,587,705 | B1 | 7/2003 | Kim | 600/347 |
| 6,589,260 | B1 | 7/2003 | Schmelzeisen-Redeker | 606/181 |
| 6,589,261 | B1 | 7/2003 | Abulhaj | 606/181 |
| 6,591,125 | B1 | 7/2003 | Buse | 600/347 |
| 6,592,745 | B1 | 7/2003 | Feldman | 205/777.5 |
| 6,595,919 | B2 | 7/2003 | Berner | 600/365 |
| 6,599,407 | B2 | 7/2003 | Taniike | 204/403.1 |
| 6,599,693 | B1 | 7/2003 | Webb | 435/4 |
| 6,602,205 | B1 | 8/2003 | Erickson | 600/573 |
| 6,602,268 | B2 | 8/2003 | Kuhr | 606/181 |
| 6,602,678 | B2 | 8/2003 | Kwon | 435/14 |
| 6,604,050 | B2 | 8/2003 | Trippel | 702/19 |
| 6,607,494 | B1 | 8/2003 | Fowler | 600/570 |
| 6,607,658 | B1 | 8/2003 | Heller | 205/777.5 |
| 6,616,616 | B2 | 9/2003 | Fritz | 600/583 |
| 6,616,819 | B1 | 9/2003 | Liamos | 204/403.02 |
| 6,618,934 | B1 | 9/2003 | Feldman | 29/830 |
| 6,620,112 | B2 | 9/2003 | Klitmose | 600/583 |
| 6,623,501 | B2 | 9/2003 | Heller | 606/181 |
| 6,626,851 | B2 | 9/2003 | Hirao | 600/576 |
| 6,635,222 | B2 | 10/2003 | Kent | 422/22 |
| 6,638,772 | B1 | 10/2003 | Douglas | 436/518 |
| 6,641,533 | B2 | 11/2003 | Causey | 600/300 |
| 6,645,142 | B2 | 11/2003 | Braig | 600/300 |
| 6,645,219 | B2 | 11/2003 | Roe | 606/182 |
| 6,645,368 | B1 | 11/2003 | Beatty | 205/792 |
| 6,650,915 | B2 | 11/2003 | Routt | 600/319 |
| 6,652,720 | B1 | 11/2003 | Mansouri | 204/403.11 |
| 6,656,702 | B1 | 12/2003 | Yugawa | 435/26 |
| 6,659,966 | B2 | 12/2003 | Essenpreis | 600/583 |
| 6,660,018 | B2 | 12/2003 | Lum | 606/181 |
| 6,671,527 | B2 | 12/2003 | Peterson | 600/316 |
| 6,679,841 | B2 | 1/2004 | Bojan | 600/309 |
| 6,679,852 | B1 | 1/2004 | Schmelzeisen-Redeker | 600/583 |
| 6,706,000 | B2 | 3/2004 | Perez | 600/583 |
| 6,706,049 | B2 | 3/2004 | Moerman | 606/181 |
| 6,706,159 | B2 | 3/2004 | Moerman | 204/403.03 |
| 6,706,232 | B2 | 3/2004 | Hasegawa | 264/403.09 |
| 6,713,660 | B1 | 3/2004 | Roe | 604/361 |
| 6,719,887 | B2 | 4/2004 | Hasegawa | 204/403.09 |
| 6,719,923 | B2 | 4/2004 | Stiene | 252/511 |
| 6,721,586 | B2 | 4/2004 | Kiser | 600/345 |
| 6,723,046 | B2 | 4/2004 | Lichtenstein | 600/300 |
| 6,723,111 | B2 | 4/2004 | Abulhaj | 606/181 |
| 6,723,371 | B2 | 4/2004 | Chih-hui | 472/2.13 |
| 6,723,500 | B2 | 4/2004 | Yu | 435/4 |
| 6,726,818 | B2 | 4/2004 | Cui et al. | 204/403.01 |
| 6,733,493 | B2 | 5/2004 | Gruzdev | 606/9 |
| 6,736,777 | B2 | 5/2004 | Kim | 600/365 |
| 6,740,215 | B1 | 5/2004 | Yamamoto | 204/403.14 |
| 6,743,211 | B1 | 6/2004 | Prausnitz | 604/239 |
| 6,743,635 | B2 | 6/2004 | Neel | 436/95 |
| 6,749,618 | B2 | 6/2004 | Levaughn | 606/182 |
| 6,749,792 | B2 | 6/2004 | Olsen | 264/328.1 |
| 6,751,491 | B2 | 6/2004 | Lew | 600/345 |
| 6,752,817 | B2 | 6/2004 | Flora | 606/181 |
| 6,759,190 | B2 | 7/2004 | Lin | 435/4 |
| 6,764,496 | B2 | 7/2004 | Schraga | 606/182 |
| 6,764,581 | B1 | 7/2004 | Forrow | 204/403 |
| 6,767,441 | B1 | 7/2004 | Cai | 204/403.03 |
| 6,773,671 | B1 | 8/2004 | Lewis | 422/58 |
| 6,776,888 | B2 | 8/2004 | Yamamoto | 204/403.06 |
| 6,780,645 | B2 | 8/2004 | Hayter | 436/8 |
| 6,780,647 | B2 | 8/2004 | Fujiwara | 436/169 |
| 6,783,502 | B2 | 8/2004 | Orloff | 600/583 |
| 6,783,537 | B1 | 8/2004 | Kuhr | 606/182 |
| 6,784,274 | B2 | 8/2004 | van Antwerp | 528/77 |
| 6,786,874 | B2 | 9/2004 | Grace | 600/573 |
| 6,787,013 | B2 | 9/2004 | Chang | 204/412 |
| 6,787,109 | B2 | 9/2004 | Haar | 422/82.05 |
| 6,787,327 | B2 | 9/2004 | Ikeda | 204/403.1 |
| 6,790,599 | B1 | 9/2004 | Madou | 430/320 |
| 6,792,791 | B2 | 9/2004 | Sato | 73/1.02 |
| 6,793,632 | B2 | 9/2004 | Sohrab | 600/573 |
| 6,793,633 | B2 | 9/2004 | Douglas | 600/583 |
| 6,793,802 | B2 | 9/2004 | Lee | 205/777.5 |
| 6,797,150 | B2 | 9/2004 | Kermani | 205/777.5 |
| 6,800,488 | B2 | 10/2004 | Khan | 436/166 |
| 6,801,041 | B2 | 10/2004 | Karinka | 324/444 |
| 6,801,804 | B2 | 10/2004 | Miller | 604/20 |
| 6,802,199 | B2 | 10/2004 | Hilgers | 72/370.1 |
| 6,802,811 | B1 | 10/2004 | Slepian | 600/309 |
| 6,802,957 | B2 | 10/2004 | Jung | 205/777.5 |

| Patent | Kind | Date | Name | Class |
|---|---|---|---|---|
| 6,805,780 | B1 | 10/2004 | Ryu | 204/403.01 |
| 6,808,499 | B1 | 10/2004 | Churchill | 600/587 |
| 6,808,908 | B2 | 10/2004 | Yao | 435/181 |
| 6,808,937 | B2 | 10/2004 | Ligler | 436/518 |
| 6,809,807 | B1 | 10/2004 | Erickson | 356/213 |
| 6,811,557 | B2 | 11/2004 | Schraga | 606/182 |
| 6,811,659 | B2 | 11/2004 | Vachon | 204/224 |
| 6,811,753 | B2 | 11/2004 | Hirao | 422/101 |
| 6,811,792 | B2 | 11/2004 | Roser | 424/423 |
| 6,812,031 | B1 | 11/2004 | Carlsson | 436/52 |
| 6,814,843 | B1 | 11/2004 | Bhullar | 204/403.01 |
| 6,814,844 | B2 | 11/2004 | Bhullar | 204/403.1 |
| 6,814,845 | B2 | 11/2004 | Wilson | 204/486 |
| 6,815,186 | B2 | 11/2004 | Clark | 435/183 |
| 6,816,742 | B2 | 11/2004 | Kim | 600/345 |
| 6,818,180 | B2 | 11/2004 | Douglas | 422/58 |
| 6,821,483 | B2 | 11/2004 | Phillips | 422/58 |
| 6,823,750 | B2 | 11/2004 | Hodges | 73/864.72 |
| 6,825,047 | B1 | 11/2004 | Woudenberg | 436/518 |
| 6,827,250 | B2 | 12/2004 | Uhland | 228/110.1 |
| 6,827,829 | B2 | 12/2004 | Kawanaka | 204/403.02 |
| 6,830,551 | B1 | 12/2004 | Uchigaki | 600/584 |
| 6,830,668 | B2 | 12/2004 | Musho | 204/400 |
| 6,830,669 | B2 | 12/2004 | Miyazaki | 204/409 |
| 6,833,540 | B2 | 12/2004 | MacKenzie | 250/214 |
| 6,835,184 | B1 | 12/2004 | Sage | 604/46 |
| 6,835,553 | B2 | 12/2004 | Han | 435/14 |
| 6,837,858 | B2 | 1/2005 | Cunningham | 600/573 |
| 6,837,976 | B2 | 1/2005 | Cai | 204/403.14 |
| 6,837,988 | B2 | 1/2005 | Leong | 205/792 |
| 6,840,912 | B2 | 1/2005 | Kloepfer | 600/583 |
| 6,841,052 | B2 | 1/2005 | Musho | 204/401 |
| 6,843,254 | B2 | 1/2005 | Tapper | 128/898 |
| 6,844,149 | B2 | 1/2005 | Goldman | 435/4 |
| 6,847,451 | B2 | 1/2005 | Pugh | 356/436 |
| 6,849,052 | B2 | 2/2005 | Uchigaki | 600/584 |
| 6,849,168 | B2 | 2/2005 | Crumly | 204/416 |
| 6,849,216 | B2 | 2/2005 | Rappin | 264/134 |
| 6,850,790 | B2 | 2/2005 | Berner | 600/347 |
| 6,869,418 | B2 | 3/2005 | Marano-Ford | 604/192 |
| 6,872,200 | B2 | 3/2005 | Mann | 604/890.1 |
| 6,875,208 | B2 | 4/2005 | Santini | 604/890.1 |
| 6,875,223 | B2 | 4/2005 | Argauer | 606/181 |
| 6,875,613 | B2 | 4/2005 | Shartle | 436/63 |
| 6,878,120 | B2 | 4/2005 | Roe | 600/583 |
| 6,878,251 | B2 | 4/2005 | Hodges | 204/403.14 |
| 6,878,255 | B1 | 4/2005 | Wang | 204/452 |
| 6,878,262 | B2 | 4/2005 | Taniike | 205/777.5 |
| 6,880,968 | B1 | 4/2005 | Haar | 374/131 |
| 6,881,203 | B2 | 4/2005 | Delmore | 604/272 |
| 6,881,322 | B2 | 4/2005 | Tokunaga | 205/775 |
| 6,881,378 | B1 | 4/2005 | Zimmer | 422/58 |
| 6,881,550 | B2 | 4/2005 | Phillips | 435/14 |
| 6,881,551 | B2 | 4/2005 | Heller | 435/14 |
| 6,881,578 | B2 | 4/2005 | Otake | 436/44 |
| 6,882,940 | B2 | 4/2005 | Potts | 702/23 |
| 6,884,592 | B2 | 4/2005 | Matzinger | 435/7.1 |
| 6,885,196 | B2 | 4/2005 | Taniike | 324/444 |
| 6,885,883 | B2 | 4/2005 | Parris | 600/347 |
| 6,887,239 | B2 | 5/2005 | Elstrom | 606/41 |
| 6,887,253 | B2 | 5/2005 | Schraga | 606/181 |
| 6,887,254 | B1 | 5/2005 | Curie | 606/181 |
| 6,887,426 | B2 | 5/2005 | Phillips | 422/56 |
| 6,887,709 | B2 | 5/2005 | Leong | 436/8 |
| 6,889,069 | B2 | 5/2005 | Routt | 600/319 |
| 6,890,319 | B1 | 5/2005 | Crocker | 604/131 |
| 6,890,421 | B2 | 5/2005 | Ohara | 205/777.5 |
| 6,890,484 | B2 | 5/2005 | Bautista | 422/58 |
| 6,891,936 | B2 | 5/2005 | Kai | 379/106.02 |
| 6,892,085 | B2 | 5/2005 | McIvor | 600/347 |
| 6,893,396 | B2 | 5/2005 | Schulze | 600/300 |
| 6,893,545 | B2 | 5/2005 | Gotoh | 204/403.5 |
| 6,893,552 | B1 | 5/2005 | Wang | 205/777.5 |
| 6,895,263 | B2 | 5/2005 | Shin | 600/316 |
| 6,895,264 | B2 | 5/2005 | Rice | 600/319 |
| 6,895,265 | B2 | 5/2005 | Silver | 600/345 |
| 6,896,793 | B2 | 5/2005 | Erdosy | 205/775 |
| 6,897,788 | B2 | 5/2005 | Khair | 340/870.16 |
| 6,902,905 | B2 | 6/2005 | Burson | 435/14 |
| 6,904,301 | B2 | 6/2005 | Raskas | 600/310 |
| 6,905,733 | B2 | 6/2005 | Russel | 427/393.5 |
| 6,908,008 | B2 | 6/2005 | Pugh | 221/135 |
| 6,908,535 | B2 | 6/2005 | Rankin | 204/406 |
| 6,908,591 | B2 | 6/2005 | MacPhee | 422/22 |
| 6,908,593 | B1 | 6/2005 | Shartle | 422/58 |
| 6,911,130 | B2 | 6/2005 | Brenneman | 204/400 |
| 6,911,131 | B2 | 6/2005 | Miyazaki | 204/403.14 |
| 6,911,621 | B2 | 6/2005 | Bhullar | 219/121.69 |
| 6,916,410 | B2 | 7/2005 | Katsuki | 204/403 |
| 6,918,918 | B1 | 7/2005 | Schraga | 606/182 |
| 6,922,576 | B2 | 7/2005 | Raskas | 600/316 |
| 6,922,578 | B2 | 7/2005 | Eppstein | 600/347 |
| 6,923,764 | B2 | 8/2005 | Aceti | 600/309 |
| 6,923,894 | B2 | 8/2005 | Huang | 204/403.06 |
| 6,923,936 | B2 | 8/2005 | Swanson | 422/22 |
| 6,924,093 | B2 | 8/2005 | Haviland | 435/4 |
| 6,925,317 | B1 | 8/2005 | Samuels | 600/344 |
| 6,925,393 | B1 | 8/2005 | Kalatz | 702/27 |
| 6,929,649 | B2 | 8/2005 | Pugh | 606/182 |
| 6,929,650 | B2 | 8/2005 | Fukuzawa | 606/182 |
| 6,931,327 | B2 | 8/2005 | Goode | 702/22 |
| 6,931,328 | B2 | 8/2005 | Braig | 702/23 |
| 6,939,310 | B2 | 9/2005 | Matzinger | 600/573 |
| 6,939,312 | B2 | 9/2005 | Hodges | 600/583 |
| 6,939,450 | B2 | 9/2005 | Karinka | 204/409 |
| 6,940,591 | B2 | 9/2005 | Sopp | 356/244 |
| 6,942,518 | B2 | 9/2005 | Liamos | 439/495 |
| 6,942,769 | B2 | 9/2005 | Cheng | 204/400 |
| 6,942,770 | B2 | 9/2005 | Cai | 204/403.04 |
| 6,944,486 | B2 | 9/2005 | Braig | 600/310 |
| 6,945,943 | B2 | 9/2005 | Pugh | 600/584 |
| 6,946,067 | B2 | 9/2005 | Hodges | 205/792 |
| 6,946,098 | B2 | 9/2005 | Miekka | 422/22 |
| 6,946,299 | B2 | 9/2005 | Neel | 436/95 |
| 6,949,111 | B2 | 9/2005 | Schraga | 606/182 |
| 6,949,221 | B2 | 9/2005 | Kiser | 422/56 |
| 6,951,631 | B1 | 10/2005 | Catt | 422/56 |
| 6,951,728 | B2 | 10/2005 | Qian | 435/14 |
| 6,952,603 | B2 | 10/2005 | Gerber | 600/310 |
| 6,952,604 | B2 | 10/2005 | DeNuzzio | 600/345 |
| 6,953,693 | B2 | 10/2005 | Neel | 436/149 |
| 6,954,662 | B2 | 10/2005 | Freger | 600/316 |
| 6,958,072 | B2 | 10/2005 | Schraga | 606/182 |
| 6,958,129 | B2 | 10/2005 | Galen | 422/57 |
| 6,958,809 | B2 | 10/2005 | Sterling | 356/39 |
| 6,959,211 | B2 | 10/2005 | Rule | 600/310 |
| 6,959,247 | B2 | 10/2005 | Neel | 702/19 |
| 6,960,287 | B2 | 11/2005 | Charlton | 205/775 |
| 6,960,289 | B2 | 11/2005 | Hodges | 205/778 |
| 6,964,871 | B2 | 11/2005 | Bell | 436/95 |
| 6,965,791 | B1 | 11/2005 | Hitchcock | 600/345 |
| 6,966,880 | B2 | 11/2005 | Boecker | 600/583 |
| 6,966,977 | B2 | 11/2005 | Hasegawa | 204/403.07 |
| 6,967,105 | B2 | 11/2005 | Nomura | 436/169 |
| 6,968,375 | B1 | 11/2005 | Brown | 709/224 |
| 6,969,359 | B2 | 11/2005 | Duchon | 600/583 |
| 6,969,450 | B2 | 11/2005 | Taniike | 204/403.01 |
| 6,969,451 | B2 | 11/2005 | Shin | 204/412 |
| 6,973,706 | B2 | 12/2005 | Say | 29/595 |
| 6,975,893 | B2 | 12/2005 | Say | 600/347 |
| 6,977,032 | B2 | 12/2005 | Hasegawa | 204/403.05 |
| 6,979,544 | B2 | 12/2005 | Keen | 435/6 |
| 6,979,571 | B2 | 12/2005 | Modzelewski | 436/164 |
| 6,982,027 | B2 | 1/2006 | Yagi | 204/403.06 |
| 6,983,176 | B2 | 1/2006 | Gardner | 600/310 |
| 6,983,177 | B2 | 1/2006 | Rule | 600/310 |

| Patent | Date | Name | Class |
|---|---|---|---|
| 6,984,307 B2 | 1/2006 | Zweig | 205/777.5 |
| 6,986,777 B2 | 1/2006 | Kim | 606/182 |
| 6,986,869 B2 | 1/2006 | Tuohy | 422/56 |
| 6,988,996 B2 | 1/2006 | Roe | 600/584 |
| 6,989,243 B2 | 1/2006 | Yani | 435/14 |
| 6,989,891 B2 | 1/2006 | Braig | 356/39 |
| 6,990,365 B1 | 1/2006 | Parker | 600/328 |
| 6,990,366 B2 | 1/2006 | Say | 600/345 |
| 6,990,367 B2 | 1/2006 | Kiser | 600/345 |
| 6,990,849 B2 | 1/2006 | Bohm | 73/53.01 |
| 6,991,918 B2 | 1/2006 | Keith | 435/31 |
| 6,991,940 B2 | 1/2006 | Carroll | 436/514 |
| 6,994,825 B2 | 2/2006 | Haviland | 422/58 |
| 6,997,317 B2 | 2/2006 | Catelli | 206/438 |
| 6,997,343 B2 | 2/2006 | May | 221/232 |
| 6,997,344 B2 | 2/2006 | Brown | 221/258 |
| 6,997,936 B2 | 2/2006 | Marshall | 606/181 |
| 6,998,247 B2 | 2/2006 | Monfre | 435/14 |
| 6,998,248 B2 | 2/2006 | Yani | 435/14 |
| 6,999,810 B2 | 2/2006 | Berner | 600/345 |
| 7,001,343 B2 | 2/2006 | Erickson | 600/573 |
| 7,001,344 B2 | 2/2006 | Freeman | 600/583 |
| 7,003,337 B2 | 2/2006 | Harjunmaa | 600/316 |
| 7,003,340 B2 | 2/2006 | Say | 600/345 |
| 7,003,341 B2 | 2/2006 | Say | 600/345 |
| 7,004,928 B2 | 2/2006 | Aceti | 604/191 |
| 7,005,048 B1 | 2/2006 | Watanabe | 204/403.04 |
| 7,005,273 B2 | 2/2006 | Heller | 435/25 |
| 7,005,459 B2 | 2/2006 | Hekal | 523/102 |
| 7,005,857 B2 | 2/2006 | Stiene | 324/449 |
| 7,006,857 B2 | 2/2006 | Braig | 600/310 |
| 7,006,858 B2 | 2/2006 | Silver | 600/345 |
| 7,008,384 B2 | 3/2006 | Tapper | 600/573 |
| 7,010,432 B2 | 3/2006 | Kermani | 702/19 |
| 7,011,630 B2 | 3/2006 | Desai | 600/309 |
| 7,011,954 B2 | 3/2006 | Ouyang | 435/7.9 |
| 7,014,615 B2 | 3/2006 | Erickson | 600/573 |
| 7,015,262 B2 | 3/2006 | Leong | 523/205 |
| 7,016,713 B2 | 3/2006 | Gardner | 600/310 |
| 7,018,568 B2 | 3/2006 | Tierney | 252/511 |
| 7,018,848 B2 | 3/2006 | Douglas | 436/524 |
| 7,022,217 B2 | 4/2006 | Hodges | 205/777.5 |
| 7,022,218 B2 | 4/2006 | Taniike | 205/777.5 |
| 7,022,286 B2 | 4/2006 | Lemke | 422/67 |
| 7,024,236 B2 | 4/2006 | Ford | 600/345 |
| 7,024,248 B2 | 4/2006 | Penner | 607/60 |
| 7,024,399 B2 | 4/2006 | Sumner | 706/45 |
| 7,025,425 B2 | 4/2006 | Kovatchev | 300/365 |
| 7,025,774 B2 * | 4/2006 | Freeman et al. | 606/181 |
| 7,027,848 B2 | 4/2006 | Robinson | 600/310 |
| 7,029,444 B2 | 4/2006 | Shin | 600/365 |
| 7,033,322 B2 | 4/2006 | Silver | 600/486 |
| 7,033,371 B2 | 4/2006 | Alden | 606/181 |
| 7,039,560 B2 | 5/2006 | Kawatahara | 702/187 |
| 7,041,057 B1 | 5/2006 | Faupel | 600/365 |
| 7,041,063 B2 | 5/2006 | Abreu | 600/549 |
| 7,041,068 B2 | 5/2006 | Freeman | 600/583 |
| 7,041,254 B2 | 5/2006 | Haviland | 422/58 |
| 7,041,468 B2 | 5/2006 | Drucker | 435/14 |
| 7,043,287 B1 | 5/2006 | Khalil | 600/310 |
| 7,044,911 B2 | 5/2006 | Drinan | 600/300 |
| 7,045,054 B1 | 5/2006 | Buck | 205/778 |
| 7,045,097 B2 | 5/2006 | Kovacs | 422/82.08 |
| 7,045,310 B2 | 5/2006 | Buck | 435/7.93 |
| 7,045,361 B2 | 5/2006 | Heiss | 436/172 |
| 7,047,070 B2 | 5/2006 | Wilkinson | 604/20 |
| 7,047,795 B2 | 5/2006 | Sato | 73/64.56 |
| 7,049,130 B2 | 5/2006 | Carroll | 435/287.2 |
| 7,050,843 B2 | 5/2006 | Shartle | 600/345 |
| 7,051,495 B2 | 5/2006 | Lang | 53/475 |
| 7,052,268 B2 | 5/2006 | Powell | 425/542 |
| 7,052,591 B2 | 5/2006 | Gao | 204/490 |
| 7,052,652 B2 | 5/2006 | Zanzucchi | 422/82.05 |
| 7,052,864 B2 | 5/2006 | Durkop | 435/25 |
| 7,054,682 B2 | 5/2006 | Young | 604/20 |
| 7,054,759 B2 | 5/2006 | Fukunaga | 702/23 |
| D523,555 S | 6/2006 | Loerwald | D24/146 |
| 7,056,425 B2 | 6/2006 | Hasegawa | 204/403.04 |
| 7,056,495 B2 | 6/2006 | Roser | 424/45 |
| 7,058,437 B2 | 6/2006 | Buse | 600/347 |
| 7,060,059 B2 | 6/2006 | Keith | 604/504 |
| 7,060,192 B2 | 6/2006 | Yuzhakov | 216/11 |
| 7,061,593 B2 | 6/2006 | Braig | 356/39 |
| 7,063,234 B2 | 6/2006 | Giraud | 221/271 |
| 7,063,774 B2 | 6/2006 | Bhullar | 204/403.02 |
| 7,063,775 B2 | 6/2006 | Yamaoka | 204/403.06 |
| 7,063,776 B2 | 6/2006 | Huang | 204/403.14 |
| 7,066,884 B2 | 6/2006 | Custer | 600/309 |
| 7,066,885 B2 | 6/2006 | Erickson | 600/309 |
| 7,070,564 B2 | 7/2006 | Matzinger | 600/300 |
| 7,070,680 B2 | 7/2006 | Bae | 204/403.04 |
| 7,073,246 B2 | 7/2006 | Bhullar | 29/595 |
| 7,074,307 B2 | 7/2006 | Simpson | 204/403.04 |
| 7,074,308 B2 | 7/2006 | Mao | 204/403.14 |
| 7,077,328 B2 | 7/2006 | Krishnaswamy | 235/472.01 |
| 7,077,828 B2 | 7/2006 | Kuhr | 604/207 |
| 7,078,480 B2 | 7/2006 | Nagel | 530/322 |
| 7,081,188 B1 | 7/2006 | Cho | 204/403.04 |
| 7,083,712 B2 | 8/2006 | Morita | 205/775 |
| 7,086,277 B2 | 8/2006 | Tess | 73/53.01 |
| 7,087,149 B1 | 8/2006 | Muguruma | 205/778 |
| 7,090,764 B2 | 8/2006 | Iyengar | 205/775 |
| 7,096,053 B2 | 8/2006 | Loeb | 600/317 |
| 7,096,124 B2 | 8/2006 | Sterling | 702/23 |
| 7,097,631 B2 | 8/2006 | Trautman | 604/46 |
| 7,098,038 B2 | 8/2006 | Fukuoka | 436/164 |
| 7,103,578 B2 | 9/2006 | Beck | 705/75 |
| 7,105,066 B2 | 9/2006 | Beck | 606/182 |
| 7,107,253 B1 | 9/2006 | Sumner | 706/45 |
| 7,108,680 B2 | 9/2006 | Rohr | 604/151 |
| 7,108,778 B2 | 9/2006 | Simpson | 205/778 |
| 7,109,271 B2 | 9/2006 | Liu | 525/283 |
| 7,110,112 B2 | 9/2006 | Uchida | 356/364 |
| 7,110,803 B2 | 9/2006 | Shults | 600/347 |
| 7,112,265 B1 | 9/2006 | McAleer | 204/403.09 |
| 7,112,451 B2 | 9/2006 | Takahashi | 436/514 |
| 7,115,362 B2 | 10/2006 | Douglas | 435/4 |
| 7,118,351 B2 | 10/2006 | Effenhauser | 417/208 |
| 7,118,667 B2 | 10/2006 | Lee | 205/777.5 |
| 7,118,668 B1 | 10/2006 | Edelbrock | 205/777.5 |
| 7,118,916 B2 | 10/2006 | Matzinger | 436/34 |
| 7,118,919 B2 | 10/2006 | Yatscoff | 436/56 |
| 7,120,483 B2 | 10/2006 | Russell | 600/345 |
| 7,122,102 B2 | 10/2006 | Wogoman | 204/400 |
| 7,122,110 B2 | 10/2006 | Deng | 205/777.5 |
| 7,122,111 B2 | 10/2006 | Tokunaga | 205/792 |
| 7,125,481 B2 | 10/2006 | Musho | 205/775 |
| 7,129,038 B2 | 10/2006 | Gopalan | 435/4 |
| RE39,390 E | 11/2006 | Hasegawa | 204/403.09 |
| D531,725 S | 11/2006 | Loerwald | D24/146 |
| 7,131,342 B2 | 11/2006 | Hodges | 73/864.72 |
| 7,131,984 B2 | 11/2006 | Sato | 606/182 |
| 7,132,041 B2 | 11/2006 | Deng | 205/777.5 |
| 7,133,710 B2 | 11/2006 | Acosta | 600/316 |
| 7,134,999 B2 | 11/2006 | Brauker | 600/309 |
| 7,135,100 B1 | 11/2006 | Lau | 204/403.14 |
| 7,137,957 B2 | 11/2006 | Erickson | 600/573 |
| 7,138,041 B2 | 11/2006 | Su | 204/403.04 |
| 7,138,089 B2 | 11/2006 | Aitken | 422/82.01 |
| 7,141,058 B2 | 11/2006 | Briggs | 606/181 |
| 7,144,404 B2 | 12/2006 | Whitson | 606/181 |
| 7,144,485 B2 | 12/2006 | Hsu | 204/403.02 |
| 7,144,495 B2 | 12/2006 | Teodorezyk | 205/792 |
| 7,144,496 B2 | 12/2006 | Meserol | 205/792 |
| 7,147,825 B2 | 12/2006 | Matsuda | 422/58 |
| 7,150,755 B2 | 12/2006 | Levaughn | 606/181 |

| | | | | | | |
|---|---|---|---|---|---|---|
| 7,150,975 B2 | 12/2006 | Tamada | 435/14 | 2003/0106810 A1 | 6/2003 | Douglas | 205/777.5 |
| 7,150,995 B2 | 12/2006 | Xie | 436/67 | 2003/0109777 A1 | 6/2003 | Kloepfer | 600/367 |
| 7,153,696 B2 | 12/2006 | Fukuoka | 436/164 | 2003/0111357 A1 | 6/2003 | Black | 205/775 |
| 7,155,371 B2 | 12/2006 | Kawatahara | 702/187 | 2003/0113827 A1 | 6/2003 | Burkoth | 435/14 |
| 7,160,251 B2 | 1/2007 | Neel | 600/365 | 2003/0116447 A1 | 6/2003 | Sturridge | 205/777.5 |
| 7,160,313 B2 | 1/2007 | Galloway | 606/167 | 2003/0135333 A1 | 7/2003 | Aceti | 702/31 |
| 7,163,616 B2 | 1/2007 | Vreeke | 205/777.5 | 2003/0139653 A1 | 7/2003 | Manser | 600/300 |
| 7,166,074 B2 | 1/2007 | Reghabi | 600/365 | 2003/0143113 A2 | 7/2003 | Yuzhakov | 422/56 |
| 7,167,734 B2 | 1/2007 | Khalil | 600/310 | 2003/0144608 A1 | 7/2003 | Kojima | 600/583 |
| 7,167,818 B2 | 1/2007 | Brown | 703/11 | 2003/0144609 A1 | 7/2003 | Kennedy | 600/583 |
| 7,344,507 B2 * | 3/2008 | Briggs et al. | 600/583 | 2003/0146110 A1 | 8/2003 | Karinka | 205/777.5 |
| 2001/0011157 A1 | 8/2001 | Latterell | 600/576 | 2003/0149348 A1 | 8/2003 | Raskas | 600/310 |
| 2001/0016682 A1 | 8/2001 | Berner | 600/345 | 2003/0149377 A1 | 8/2003 | Erickson | 600/573 |
| 2001/0017269 A1 | 8/2001 | Heller | 205/777.5 | 2003/0153900 A1 | 8/2003 | Aceti | 604/890.1 |
| 2001/0027328 A1 | 10/2001 | Lum | 606/186 | 2003/0159944 A1 | 8/2003 | Pottgen | 205/777.5 |
| 2001/0031931 A1 | 10/2001 | Cunningham et al. | 600/573 | 2003/0163351 A1 | 8/2003 | Brown | 705/2 |
| 2001/0054319 A1 | 12/2001 | Heller | 73/849 | 2003/0178322 A1 | 9/2003 | Iyengar | 205/775 |
| 2002/0002344 A1 | 1/2002 | Douglas et al. | 600/583 | 2003/0191415 A1 | 10/2003 | Moerman | 600/584 |
| 2002/0004196 A1 | 1/2002 | Whitson | 435/4 | 2003/0195435 A1 | 10/2003 | Williams | 600/583 |
| 2002/0016606 A1 | 2/2002 | Moerman | 606/181 | 2003/0195540 A1 | 10/2003 | Moerman | 606/181 |
| 2002/0019748 A1 | 2/2002 | Brown | 705/2 | 2003/0199744 A1 | 10/2003 | Buse | 600/347 |
| 2002/0025469 A1 | 2/2002 | Heller | 429/43 | 2003/0199789 A1 | 10/2003 | Boecker | 600/575 |
| 2002/0029058 A1 | 3/2002 | Levaughn | 606/181 | 2003/0199790 A1 | 10/2003 | Boecker | 600/576 |
| 2002/0040230 A1 | 4/2002 | Kuhr | 606/181 | 2003/0199791 A1 | 10/2003 | Boecker | 600/576 |
| 2002/0042090 A1 | 4/2002 | Heller | 435/14 | 2003/0199891 A1 | 10/2003 | Argauer | 606/181 |
| 2002/0042594 A1 | 4/2002 | Lum Paul et al. | | 2003/0199893 A1 | 10/2003 | Boecker | 606/181 |
| 2002/0044890 A1 | 4/2002 | Black | 422/56 | 2003/0199894 A1 | 10/2003 | Boecker | 606/181 |
| 2002/0052618 A1 | 5/2002 | Haar et al. | 606/181 | 2003/0199895 A1 | 10/2003 | Boecker | 606/181 |
| 2002/0053523 A1 | 5/2002 | Liamos | 205/787 | 2003/0199896 A1 | 10/2003 | Boecker | 606/181 |
| 2002/0057993 A1 | 5/2002 | Maisey | 422/82.01 | 2003/0199897 A1 | 10/2003 | Boecker | 606/181 |
| 2002/0076349 A1 | 6/2002 | Aitken | 422/58 | 2003/0199898 A1 | 10/2003 | Boecker | 606/181 |
| 2002/0078091 A1 | 6/2002 | Vu | 707/513 | 2003/0199899 A1 | 10/2003 | Boecker | 606/181 |
| 2002/0081559 A1 | 6/2002 | Brown | 434/307 R | 2003/0199900 A1 | 10/2003 | Boecker | 606/181 |
| 2002/0081588 A1 | 6/2002 | Lumley-Woodyear | 435/6 | 2003/0199901 A1 | 10/2003 | Boecker | 606/181 |
| 2002/0082543 A1 | 6/2002 | Park et al. | 604/21 | 2003/0199902 A1 | 10/2003 | Boecker | 606/181 |
| 2002/0084196 A1 | 7/2002 | Liamos | 205/792 | 2003/0199903 A1 | 10/2003 | Boecker | 606/181 |
| 2002/0087056 A1 | 7/2002 | Aceti | | 2003/0199904 A1 | 10/2003 | Boecker | 606/181 |
| 2002/0092612 A1 | 7/2002 | Davies | 156/292 | 2003/0199905 A1 | 10/2003 | Boecker | 606/181 |
| 2002/0103499 A1 | 8/2002 | Perez et al. | 606/182 | 2003/0199906 A1 | 10/2003 | Boecker | 606/181 |
| 2002/0120216 A1 | 8/2002 | Fritz | 600/583 | 2003/0199907 A1 | 10/2003 | Boecker | 606/181 |
| 2002/0120261 A1 | 8/2002 | Morris | 606/41 | 2003/0199908 A1 | 10/2003 | Boecker | 606/181 |
| 2002/0130042 A1 | 9/2002 | Moerman | 204/403.01 | 2003/0199909 A1 | 10/2003 | Boecker | 606/181 |
| 2002/0133377 A1 | 9/2002 | Brown | 705/3 | 2003/0199910 A1 | 10/2003 | Boecker | 606/181 |
| 2002/0136667 A1 | 9/2002 | Subramanian | 422/100 | 2003/0199911 A1 | 10/2003 | Boecker | 606/181 |
| 2002/0136863 A1 | 9/2002 | Subramanian | 428/156 | 2003/0199912 A1 | 10/2003 | Pugh | 606/182 |
| 2002/0137998 A1 | 9/2002 | Smart | 600/347 | 2003/0201194 A1 | 10/2003 | Heller | 205/777.5 |
| 2002/0138040 A1 | 9/2002 | Flora | 604/116 | 2003/0203352 A1 | 10/2003 | Haviland | 435/4 |
| 2002/0148739 A2 | 10/2002 | Liamos | 205/787 | 2003/0206828 A1 | 11/2003 | Bell | 422/44 |
| 2002/0160520 A1 | 10/2002 | Orloff | 436/72 | 2003/0208140 A1 | 11/2003 | Pugh | 600/584 |
| 2002/0161289 A1 | 10/2002 | Hopkins | 600/322 | 2003/0212344 A1 | 11/2003 | Yuzhakov | 600/583 |
| 2002/0168290 A1 | 11/2002 | Yuzhakov | 422/56 | 2003/0212345 A1 | 11/2003 | McAllister | 600/584 |
| 2002/0176984 A1 | 11/2002 | Smart | 428/336 | 2003/0212346 A1 | 11/2003 | McAllister | 600/584 |
| 2002/0177761 A1 | 11/2002 | Orloff | 600/309 | 2003/0212347 A1 | 11/2003 | Sohrab | 600/584 |
| 2002/0188224 A1 | 12/2002 | Roe | 600/584 | 2003/0212423 A1 | 11/2003 | Pugh | 606/181 |
| 2003/0018282 A1 | 1/2003 | Effenhauser | 600/583 | 2003/0212424 A1 | 11/2003 | Briggs | 606/181 |
| 2003/0018300 A1 | 1/2003 | Duchon | 604/164.01 | 2003/0212579 A1 | 11/2003 | Brown | 705/2 |
| 2003/0028125 A1 | 2/2003 | Yuzhakov | | 2003/0216767 A1 | 11/2003 | List | 606/181 |
| 2003/0028126 A1 | 2/2003 | List | 600/583 | 2003/0217918 A1 | 11/2003 | Davies | 204/403.14 |
| 2003/0050537 A1 | 3/2003 | Wessel | 600/300 | 2003/0220552 A1 | 11/2003 | Reghabi | 600/365 |
| 2003/0050573 A1 | 3/2003 | Kuhr | 600/567 | 2003/0220663 A1 | 11/2003 | Fletcher | 606/182 |
| 2003/0050656 A1 | 3/2003 | Schraga | 606/182 | 2003/0223906 A1 | 12/2003 | McAllister | 422/58 |
| 2003/0060730 A1 | 3/2003 | Perez | 600/576 | 2003/0225317 A1 | 12/2003 | Schell | 600/300 |
| 2003/0069753 A1 | 4/2003 | Brown | 705/2 | 2003/0225429 A1 | 12/2003 | Garthe | 606/182 |
| 2003/0073089 A1 | 4/2003 | Mauze | 435/6 | 2003/0225430 A1 | 12/2003 | Schraga | 606/182 |
| 2003/0073229 A1 | 4/2003 | Greenstein | 435/287.2 | 2003/0228637 A1 | 12/2003 | Wang | 435/7.9 |
| 2003/0073931 A1 | 4/2003 | Boecker | 600/573 | 2003/0229514 A2 | 12/2003 | Brown | 705/2 |
| 2003/0083685 A1 | 5/2003 | Freeman et al. | 606/181 | 2003/0232370 A1 | 12/2003 | Trifiro | 435/6 |
| 2003/0083686 A1 | 5/2003 | Freeman | 606/181 | 2003/0233055 A1 | 12/2003 | Erickson | 600/573 |
| 2003/0088160 A1 | 5/2003 | Halleck | 600/300 | 2003/0233112 A1 | 12/2003 | Alden et al. | 606/181 |
| 2003/0088191 A1 | 5/2003 | Freeman et al. | 600/583 | 2003/0233113 A1 | 12/2003 | Alden et al. | 606/182 |
| 2003/0089730 A1 | 5/2003 | May | 221/232 | 2004/0006285 A1 | 1/2004 | Douglas | 600/583 |
| 2003/0093010 A1 | 5/2003 | Essenpreis | 600/583 | 2004/0007585 A1 | 1/2004 | Griffith | 221/232 |
| 2003/0100040 A1 | 5/2003 | Bonnecaze | 435/14 | 2004/0009100 A1 | 1/2004 | Simons | 422/102 |

| | | | | | | |
|---|---|---|---|---|---|---|
| 2004/0010279 A1 | 1/2004 | Freeman ............... 606/182 | | 2004/0171968 A1 | 9/2004 | Katsuki ............... 600/583 |
| 2004/0015064 A1 | 1/2004 | Parsons ............... 600/347 | | 2004/0172000 A1 | 9/2004 | Roe ............... 604/361 |
| 2004/0019250 A1 | 1/2004 | Catelli ............... 600/1 | | 2004/0173472 A1 | 9/2004 | Jung ............... 205/777.5 |
| 2004/0019259 A1 | 1/2004 | Brown ............... 600/300 | | 2004/0173488 A1 | 9/2004 | Griffin ............... 206/363 |
| 2004/0026243 A1 | 2/2004 | Davies ............... 204/403.14 | | 2004/0176705 A1 | 9/2004 | Stevens ............... 600/584 |
| 2004/0030353 A1 | 2/2004 | Schmelzeisen-Redeker . 606/201 | | 2004/0176732 A1 | 9/2004 | Frazier ............... 604/345 |
| 2004/0031682 A1 | 2/2004 | Wilsey ............... 204/403.1 | | 2004/0178066 A1 | 9/2004 | Miyazaki ............... 204/403.01 |
| 2004/0034318 A1 | 2/2004 | Fritz ............... 604/19 | | 2004/0178067 A1 | 9/2004 | Miyazaki ............... 204/403.1 |
| 2004/0038045 A1 | 2/2004 | Smart ............... 428/446 | | 2004/0178216 A1 | 9/2004 | Brickwood ............... 221/268 |
| 2004/0039303 A1 | 2/2004 | Wurster ............... 600/584 | | 2004/0180379 A1 | 9/2004 | van Duyne ............... 435/7.1 |
| 2004/0039342 A1 | 2/2004 | Eppstein ............... 604/200 | | 2004/0182703 A1 | 9/2004 | Bell ............... 204/403.11 |
| 2004/0039407 A1 | 2/2004 | Schraga ............... 606/181 | | 2004/0185568 A1 | 9/2004 | Matsumoto ............... 436/8 |
| 2004/0039408 A1 | 2/2004 | Abulhaj ............... 606/181 | | 2004/0186359 A1 | 9/2004 | Beaudoin ............... 600/310 |
| 2004/0049219 A1 | 3/2004 | Briggs ............... 606/181 | | 2004/0186394 A1 | 9/2004 | Roe ............... 600/598 |
| 2004/0049220 A1 | 3/2004 | Boecker ............... 606/181 | | 2004/0186500 A1 | 9/2004 | Koilke ............... 606/181 |
| 2004/0050694 A1 | 3/2004 | Yang ............... 204/403.02 | | 2004/0193201 A1 | 9/2004 | Kim ............... 606/181 |
| 2004/0054267 A1 | 3/2004 | Feldman ............... 600/316 | | 2004/0193377 A1 | 9/2004 | Brown ............... 702/19 |
| 2004/0055898 A1 | 3/2004 | Heller ............... 205/777.5 | | 2004/0194302 A1 | 10/2004 | Bhullar ............... 29/847 |
| 2004/0059256 A1 | 3/2004 | Perez ............... 600/583 | | 2004/0197231 A1 | 10/2004 | Katsuki ............... 422/68.1 |
| 2004/0060818 A1 | 4/2004 | Feldman ............... 204/403.01 | | 2004/0197821 A1 | 10/2004 | Bauer ............... 437/7.1 |
| 2004/0061841 A1 | 4/2004 | Black ............... 355/30 | | 2004/0199062 A1 | 10/2004 | Petersson ............... 600/316 |
| 2004/0064068 A1 | 4/2004 | DeNuzzio ............... 600/583 | | 2004/0199409 A1 | 10/2004 | Brown ............... 705/3 |
| 2004/0087990 A1 | 5/2004 | Boecker ............... 606/181 | | 2004/0200720 A1 | 10/2004 | Musho ............... 204/403.01 |
| 2004/0092842 A1 | 5/2004 | Boecker ............... 600/575 | | 2004/0200721 A1 | 10/2004 | Bhullar ............... 204/403.01 |
| 2004/0092994 A1 | 5/2004 | Briggs ............... 606/181 | | 2004/0202576 A1 | 10/2004 | Aceti ............... 422/82.05 |
| 2004/0092995 A1 | 5/2004 | Boecker ............... 606/181 | | 2004/0204662 A1 | 10/2004 | Perez ............... 600/583 |
| 2004/0096991 A1 | 5/2004 | Zhang ............... 436/518 | | 2004/0206625 A1 | 10/2004 | Bhullar ............... 204/403.1 |
| 2004/0098009 A1 | 5/2004 | Boecker ............... 606/181 | | 2004/0206636 A1 | 10/2004 | Hodges ............... 205/792 |
| 2004/0098010 A1 | 5/2004 | Davison ............... 606/181 | | 2004/0206658 A1 | 10/2004 | Hammerstedt ............ 206/524.1 |
| 2004/0102803 A1 | 5/2004 | Boecker ............... 606/183 | | 2004/0209307 A1 | 10/2004 | Valkirs ............... 435/7.1 |
| 2004/0106855 A1 | 6/2004 | Brown ............... 600/301 | | 2004/0209350 A1 | 10/2004 | Sakata ............... 435/287.1 |
| 2004/0106858 A1 | 6/2004 | Say ............... 600/345 | | 2004/0209354 A1 | 10/2004 | Mathies ............... 435/287.2 |
| 2004/0106859 A1 | 6/2004 | Say ............... 600/345 | | 2004/0210279 A1 | 10/2004 | Gruzdev ............... 607/89 |
| 2004/0106860 A1 | 6/2004 | Say ............... 600/345 | | 2004/0211666 A1 | 10/2004 | Pamidi ............... 204/403.01 |
| 2004/0106904 A1 | 6/2004 | Gonnelli ............... 604/173 | | 2004/0214253 A1 | 10/2004 | Paek ............... 435/7.92 |
| 2004/0106941 A1 | 6/2004 | Roe ............... 606/181 | | 2004/0215224 A1 | 10/2004 | Sakata ............... 606/181 |
| 2004/0107116 A1 | 6/2004 | Brown ............... 705/2 | | 2004/0215225 A1 | 10/2004 | Nakayama ............... 606/182 |
| 2004/0115754 A1 | 6/2004 | Chang ............... 435/14 | | 2004/0216516 A1 | 11/2004 | Sato ............... 73/64.56 |
| 2004/0115831 A1 | 6/2004 | Meathrel ............... 436/514 | | 2004/0217019 A1 | 11/2004 | Cai ............... 205/792 |
| 2004/0116780 A1 | 6/2004 | Brown ............... 600/300 | | 2004/0219500 A1 | 11/2004 | Brown ............... 434/307 R |
| 2004/0116829 A1 | 6/2004 | Raney ............... 600/573 | | 2004/0219535 A1 | 11/2004 | Bell ............... 435/6 |
| 2004/0117207 A1 | 6/2004 | Brown ............... 705/2 | | 2004/0220456 A1 | 11/2004 | Eppstein ............... 600/309 |
| 2004/0117208 A1 | 6/2004 | Brown ............... 705/2 | | 2004/0220495 A1 | 11/2004 | Cahir ............... 600/562 |
| 2004/0117209 A1 | 6/2004 | Brown ............... 705/2 | | 2004/0220564 A1 | 11/2004 | Ho ............... 606/47 |
| 2004/0117210 A1 | 6/2004 | Brown ............... 705/2 | | 2004/0220603 A1 | 11/2004 | Rutynowski ............... 606/181 |
| 2004/0122339 A1 | 6/2004 | Roe | | 2004/0222092 A1 | 11/2004 | Musho ............... 204/401 |
| 2004/0127818 A1 | 7/2004 | Roe ............... 600/583 | | 2004/0224369 A1 | 11/2004 | Cai ............... 435/7.7 |
| 2004/0127819 A1 | 7/2004 | Roe ............... 600/583 | | 2004/0225230 A1 | 11/2004 | Liamos ............... 600/583 |
| 2004/0127928 A1 | 7/2004 | Whitson ............... 606/181 | | 2004/0225311 A1 | 11/2004 | Levaughn ............... 606/181 |
| 2004/0127929 A1 | 7/2004 | Roe ............... 606/181 | | 2004/0225312 A1 | 11/2004 | Orloff ............... 606/182 |
| 2004/0132167 A1 | 7/2004 | Rule ............... 435/287.1 | | 2004/0230216 A1 | 11/2004 | Levaughn ............... 606/181 |
| 2004/0133125 A1 | 7/2004 | Miyashita ............... 600/573 | | 2004/0231984 A1 | 11/2004 | Lauks ............... 204/416 |
| 2004/0133127 A1 | 7/2004 | Roe ............... 600/583 | | 2004/0232009 A1 | 11/2004 | Okuda ............... 205/789 |
| 2004/0137640 A1 | 7/2004 | Hirao ............... 436/514 | | 2004/0236250 A1 | 11/2004 | Hodges ............... 600/583 |
| 2004/0138541 A1 | 7/2004 | Ward ............... 600/345 | | 2004/0236251 A1 | 11/2004 | Roe ............... 600/583 |
| 2004/0138588 A1 | 7/2004 | Saikley ............... 600/583 | | 2004/0236268 A1 | 11/2004 | Mitragotri ............... 604/20 |
| 2004/0138688 A1 | 7/2004 | Giraud ............... 606/181 | | 2004/0236362 A1 | 11/2004 | Shraga ............... 606/181 |
| 2004/0146958 A1 | 7/2004 | Bae ............... 435/14 | | 2004/0238357 A1 | 12/2004 | Bhullar ............... 204/400 |
| 2004/0154932 A1 | 8/2004 | Deng ............... 205/777.5 | | 2004/0238358 A1 | 12/2004 | Forrow ............... 204/403 |
| 2004/0157017 A1 | 8/2004 | Mauze ............... 428/35.7 | | 2004/0238359 A1 | 12/2004 | Ikeda ............... 204/403.1 |
| 2004/0157149 A1 | 8/2004 | Hofmann ............... 430/131 | | 2004/0241746 A1 | 12/2004 | Adlassnig ............... 435/7.1 |
| 2004/0157319 A1 | 8/2004 | Keen ............... 435/287.2 | | 2004/0242977 A1 | 12/2004 | Dosmann ............... 600/315 |
| 2004/0157338 A1 | 8/2004 | Burke ............... 436/147 | | 2004/0243164 A1 | 12/2004 | D'Agostino ............... 606/181 |
| 2004/0157339 A1 | 8/2004 | Burke ............... 436/149 | | 2004/0243165 A1 | 12/2004 | Koike ............... 606/181 |
| 2004/0158137 A1 | 8/2004 | Eppstein ............... 600/347 | | 2004/0245101 A1 | 12/2004 | Willner ............... 204/403 |
| 2004/0158271 A1 | 8/2004 | Hamamoto ............... 606/181 | | 2004/0248282 A1 | 12/2004 | Sobha ............... 435/287.2 |
| 2004/0161737 A1 | 8/2004 | Yang ............... 435/5 | | 2004/0248312 A1 | 12/2004 | Vreeke ............... 436/95 |
| 2004/0162473 A1 | 8/2004 | Sohrab ............... 600/345 | | 2004/0249254 A1 | 12/2004 | Racchini ............... 600/347 |
| 2004/0162474 A1 | 8/2004 | Kiser ............... 600/345 | | 2004/0249310 A1 | 12/2004 | Shartle ............... 600/583 |
| 2004/0162506 A1 | 8/2004 | Duchon ............... 600/583 | | 2004/0249311 A1 | 12/2004 | Haar ............... 600/584 |
| 2004/0162573 A1 | 8/2004 | Keheiri ............... 606/182 | | 2004/0249405 A1 | 12/2004 | Watanabe ............... 606/181 |
| 2004/0167383 A1 | 8/2004 | Kim ............... 600/365 | | 2004/0249406 A1 | 12/2004 | Griffin ............... 606/182 |
| 2004/0171057 A1 | 9/2004 | Yang ............... 435/6 | | 2004/0251131 A1 | 12/2004 | Ueno ............... 204/403 |

| Publication No. | Date | Name | Class |
|---|---|---|---|
| 2004/0253634 A1 | 12/2004 | Wang | 435/7.1 |
| 2004/0254434 A1 | 12/2004 | Goodnow | 600/365 |
| 2004/0254599 A1 | 12/2004 | Lipoma | 606/181 |
| 2004/0256228 A1 | 12/2004 | Huang | 204/434 |
| 2004/0256248 A1 | 12/2004 | Burke | 205/792 |
| 2004/0256685 A1 | 12/2004 | Chou | 257/414 |
| 2004/0258564 A1 | 12/2004 | Charlton | 422/58 |
| 2004/0260204 A1 | 12/2004 | Boecker | 600/584 |
| 2004/0260324 A1 | 12/2004 | Fukuzawa | 606/181 |
| 2004/0260325 A1 | 12/2004 | Kuhr | 606/181 |
| 2004/0260326 A1 | 12/2004 | Lipoma | 606/182 |
| 2004/0260511 A1 | 12/2004 | Burke | 702/182 |
| 2004/0267105 A1 | 12/2004 | Monfre | 600/344 |
| 2004/0267160 A9 | 12/2004 | Perez | 600/583 |
| 2004/0267229 A1 | 12/2004 | Moerman | 604/500 |
| 2004/0267299 A1 | 12/2004 | Kuriger | 606/181 |
| 2004/0267300 A1 | 12/2004 | Mace | 606/182 |
| 2005/0000806 A1 | 1/2005 | Hsieh | 203/403.1 |
| 2005/0000807 A1 | 1/2005 | Wang | 204/403.81 |
| 2005/0000808 A1 | 1/2005 | Cui | 203/403.14 |
| 2005/0003470 A1 | 1/2005 | Nelson | 435/14 |
| 2005/0004437 A1 | 1/2005 | Kaufmann | 600/300 |
| 2005/0004494 A1 | 1/2005 | Perez | 600/583 |
| 2005/0008537 A1 | 1/2005 | Mosolu | 422/56 |
| 2005/0008851 A1 | 1/2005 | Ezoe | 428/336 |
| 2005/0009191 A1 | 1/2005 | Swenson | 436/43 |
| 2005/0010090 A1 | 1/2005 | Acosta | 600/316 |
| 2005/0010093 A1 | 1/2005 | Ford | 600/345 |
| 2005/0010134 A1* | 1/2005 | Douglas et al. | 600/573 |
| 2005/0010137 A1 | 1/2005 | Hodges | 600/573 |
| 2005/0010198 A1 | 1/2005 | Marchitto | 606/9 |
| 2005/0011759 A1 | 1/2005 | Moerman | 204/403.03 |
| 2005/0013731 A1 | 1/2005 | Burke | 422/56 |
| 2005/0014997 A1 | 1/2005 | Ruchti | 600/310 |
| 2005/0015020 A1 | 1/2005 | Levaughn | 600/583 |
| 2005/0016844 A1 | 1/2005 | Burke | 204/403.1 |
| 2005/0019212 A1 | 1/2005 | Bhullar | 422/56 |
| 2005/0019219 A1 | 1/2005 | Oshiman | 422/82.12 |
| 2005/0019805 A1 | 1/2005 | Groll | 435/6 |
| 2005/0019945 A1 | 1/2005 | Groll | 436/169 |
| 2005/0019953 A1 | 1/2005 | Groll | 436/514 |
| 2005/0021066 A1 | 1/2005 | Kuhr | 606/181 |
| 2005/0027181 A1 | 2/2005 | Goode et al. | |
| 2005/0027211 A1 | 2/2005 | Kuhr | 600/583 |
| 2005/0027562 A1 | 2/2005 | Brown | 705/2 |
| 2005/0033341 A1 | 2/2005 | Vreeke | 606/181 |
| 2005/0034983 A1 | 2/2005 | Chambers | 204/403.01 |
| 2005/0036020 A1 | 2/2005 | Li | 347/100 |
| 2005/0036146 A1 | 2/2005 | Braig | 356/246 |
| 2005/0036906 A1 | 2/2005 | Katsuji | 422/58 |
| 2005/0036909 A1 | 2/2005 | Erickson | 422/61 |
| 2005/0037482 A1 | 2/2005 | Braig | 435/287 |
| 2005/0038329 A1 | 2/2005 | Morris | 600/319 |
| 2005/0038330 A1 | 2/2005 | Jansen | 600/345 |
| 2005/0038463 A1 | 2/2005 | Davar | 606/181 |
| 2005/0038464 A1 | 2/2005 | Schraga | 606/182 |
| 2005/0038465 A1 | 2/2005 | Schraga | 606/182 |
| 2005/0038674 A1 | 2/2005 | Braig | 705/2 |
| 2005/0042766 A1 | 2/2005 | Ohman | 436/174 |
| 2005/0043894 A1 | 2/2005 | Fernandez | 702/19 |
| 2005/0043965 A1 | 2/2005 | Heller | 705/2 |
| 2005/0045476 A1 | 3/2005 | Neel | 204/403.2 |
| 2005/0049473 A1 | 3/2005 | Desai et al. | 600/347 |
| 2005/0050859 A1 | 3/2005 | Coppeta | 53/471 |
| 2005/0054082 A1 | 3/2005 | Pachl | 435/287.2 |
| 2005/0059895 A1 | 3/2005 | Brown | 600/481 |
| 2005/0060194 A1 | 3/2005 | Brown | 705/2 |
| 2005/0067280 A1 | 3/2005 | Reid | 204/403.14 |
| 2005/0067737 A1 | 3/2005 | Rappin | 264/272.19 |
| 2005/0070771 A1 | 3/2005 | Rule | 600/316 |
| 2005/0070819 A1 | 3/2005 | Poux | 600/576 |
| 2005/0070945 A1 | 3/2005 | Schraga | 606/182 |
| 2005/0072670 A1 | 4/2005 | Hasegawa | 204/403.01 |
| 2005/0077176 A1 | 4/2005 | Hodges | 204/403.01 |
| 2005/0077584 A1 | 4/2005 | Uhland | 257/414 |
| 2005/0079542 A1 | 4/2005 | Cullen | 435/7.1 |
| 2005/0080652 A1 | 4/2005 | Brown | 705/2 |
| 2005/0085839 A1 | 4/2005 | Allen | 606/181 |
| 2005/0085840 A1 | 4/2005 | Yi | 606/182 |
| 2005/0086083 A1 | 4/2005 | Brown | 705/2 |
| 2005/0090754 A1 | 4/2005 | Wolf | 600/509 |
| 2005/0090850 A1 | 4/2005 | Toes | 606/182 |
| 2005/0096520 A1 | 5/2005 | Maekawa | 600/365 |
| 2005/0096565 A1 | 5/2005 | Chang | 600/584 |
| 2005/0096586 A1 | 5/2005 | Trautman | 604/46 |
| 2005/0096587 A1 | 5/2005 | Santini | 604/66 |
| 2005/0096686 A1 | 5/2005 | Allen | 606/181 |
| 2005/0098431 A1 | 5/2005 | Hodges | 204/403.01 |
| 2005/0098432 A1 | 5/2005 | Gundel | 204/403.2 |
| 2005/0098433 A1 | 5/2005 | Gundel | 204/403.2 |
| 2005/0098434 A1 | 5/2005 | Gundel | 204/403.02 |
| 2005/0100880 A1 | 5/2005 | Chang | 435/4 |
| 2005/0101841 A9 | 5/2005 | Kaylor | 600/300 |
| 2005/0101979 A1 | 5/2005 | Alden | 606/181 |
| 2005/0101980 A1 | 5/2005 | Alden | 606/181 |
| 2005/0101981 A1 | 5/2005 | Alden | 606/181 |
| 2005/0103624 A1 | 5/2005 | Bhullar | 204/403.01 |
| 2005/0106713 A1 | 5/2005 | Phan | 435/287.2 |
| 2005/0109637 A1 | 5/2005 | Iyengar | 205/775 |
| 2005/0112782 A1 | 5/2005 | Buechler | 436/518 |
| 2005/0113658 A1 | 5/2005 | Jacobson | 600/342 |
| 2005/0113717 A1 | 5/2005 | Matzinger | 600/573 |
| 2005/0114062 A1 | 5/2005 | Davies | 702/104 |
| 2005/0114154 A1 | 5/2005 | Wolkowiez | 705/1 |
| 2005/0114444 A1 | 5/2005 | Brown | 709/203 |
| 2005/0118056 A1 | 6/2005 | Swanson | 423/23 |
| 2005/0119681 A1 | 6/2005 | Marshall | 606/181 |
| 2005/0123443 A1 | 6/2005 | Fujiwara | 422/58 |
| 2005/0123680 A1 | 6/2005 | Kang | 427/248.1 |
| 2005/0124869 A1 | 6/2005 | Hefti | 600/316 |
| 2005/0125017 A1 | 6/2005 | Kudrna | 606/181 |
| 2005/0125018 A1 | 6/2005 | Galloway | 606/181 |
| 2005/0125019 A1 | 6/2005 | Kudrna | 606/182 |
| 2005/0126929 A1 | 6/2005 | Mansouri | 205/778 |
| 2005/0130248 A1 | 6/2005 | Willner | 435/14 |
| 2005/0130249 A1 | 6/2005 | Parris | 435/14 |
| 2005/0130292 A1 | 6/2005 | Ahn | 435/287.1 |
| 2005/0131286 A1 | 6/2005 | Parker | 600/328 |
| 2005/0131441 A1 | 6/2005 | Iio | 606/182 |
| 2005/0133368 A1 | 6/2005 | Davies | 204/403.01 |
| 2005/0136471 A1 | 6/2005 | Bhullar | 435/6 |
| 2005/0136501 A1 | 6/2005 | Kuriger | 435/14 |
| 2005/0136529 A1 | 6/2005 | Yang | 435/287 |
| 2005/0136550 A1 | 6/2005 | Yang | 436/514 |
| 2005/0137531 A1 | 6/2005 | Gonnelli | 604/173 |
| 2005/0137536 A1 | 6/2005 | Gonnelli | 604/264 |
| 2005/0143675 A1 | 6/2005 | Neel | 600/583 |
| 2005/0143713 A1 | 6/2005 | Delmore | 604/506 |
| 2005/0143771 A1 | 6/2005 | Stout | 606/181 |
| 2005/0145490 A1 | 7/2005 | Shinno | 204/403 |
| 2005/0145491 A1 | 7/2005 | Amano | 204/403 |
| 2005/0145520 A1 | 7/2005 | Ilo | 206/365 |
| 2005/0149088 A1 | 7/2005 | Fukuda | 606/181 |
| 2005/0149089 A1 | 7/2005 | Trissel | 606/181 |
| 2005/0150762 A1 | 7/2005 | Butters | 204/403 |
| 2005/0150763 A1 | 7/2005 | Butters | 204/403 |
| 2005/0154277 A1 | 7/2005 | Ting | 600/407 |
| 2005/0154374 A1 | 7/2005 | Hunter | 604/890 |
| 2005/0154410 A1 | 7/2005 | Conway | 606/181 |
| 2005/0154616 A1 | 7/2005 | Iliff | 705/3 |
| 2005/0158850 A1 | 7/2005 | Kubo | 435/287.2 |
| 2005/0159656 A1 | 7/2005 | Hockersmith | 600/315 |
| 2005/0159768 A1 | 7/2005 | Boehm | 606/182 |
| 2005/0164322 A1 | 7/2005 | Heller | 435/14 |
| 2005/0164329 A1 | 7/2005 | Wallace-Davis | 435/25 |
| 2005/0165285 A1 | 7/2005 | Iliff | 600/300 |

| Publication No. | Date | Name | Class |
|---|---|---|---|
| 2005/0165393 A1 | 7/2005 | Eppstein | 606/41 |
| 2005/0165622 A1 | 7/2005 | Neel | 705/2 |
| 2005/0169961 A1 | 8/2005 | Hunter | 424/423 |
| 2005/0170448 A1 | 8/2005 | Burson | 435/14 |
| 2005/0171567 A1 | 8/2005 | DeHart | 606/181 |
| 2005/0172021 A1 | 8/2005 | Brown | 709/224 |
| 2005/0172022 A1 | 8/2005 | Brown | 709/224 |
| 2005/0173245 A1 | 8/2005 | Feldman | 204/403.01 |
| 2005/0173246 A1 | 8/2005 | Hodges | 204/403.11 |
| 2005/0175509 A1 | 8/2005 | Nakaminami | 422/82.03 |
| 2005/0176084 A1 | 8/2005 | Burkoth | 435/14 |
| 2005/0176133 A1 | 8/2005 | Miyashita | 435/287.1 |
| 2005/0177071 A1 | 8/2005 | Nakayama | 600/583 |
| 2005/0177201 A1 | 8/2005 | Freeman | 607/46 |
| 2005/0177398 A1 | 8/2005 | Watanabe | 705/3 |
| 2005/0178218 A1 | 8/2005 | Montagu | 73/864.34 |
| 2005/0181010 A1 | 8/2005 | Hunter | 424/423 |
| 2005/0181497 A1 | 8/2005 | Saito | 435/287.1 |
| 2005/0182307 A1 | 8/2005 | Currie | 600/300 |
| 2005/0187439 A1 | 8/2005 | Blank | 600/310 |
| 2005/0187444 A1 | 8/2005 | Hubner | 600/322 |
| 2005/0192488 A1 | 9/2005 | Bryenton | 600/301 |
| 2005/0196821 A1 | 9/2005 | Monfre | 435/14 |
| 2005/0197666 A1 | 9/2005 | Raney | 606/181 |
| 2005/0201897 A1 | 9/2005 | Zimmer | 422/82.05 |
| 2005/0202567 A1 | 9/2005 | Zanzucchi | 436/95 |
| 2005/0203358 A1 | 9/2005 | Monfre | 600/331 |
| 2005/0203364 A1 | 9/2005 | Monfre | 600/365 |
| 2005/0204939 A1 | 9/2005 | Krejci | 101/129 |
| 2005/0205422 A1 | 9/2005 | Moser | 204/403.06 |
| 2005/0205816 A1 | 9/2005 | Hayenga | 251/61.1 |
| 2005/0209515 A1 | 9/2005 | Hockersmith | 600/316 |
| 2005/0209564 A1 | 9/2005 | Bonner | 604/173 |
| 2005/0209625 A1 | 9/2005 | Chan | 606/181 |
| 2005/0211571 A1 | 9/2005 | Schulein | 205/777.5 |
| 2005/0211572 A1 | 9/2005 | Buck | 205/778 |
| 2005/0214881 A1 | 9/2005 | Azarnia | 435/7.92 |
| 2005/0214892 A1 | 9/2005 | Kovatchev | 435/25 |
| 2005/0215871 A1 | 9/2005 | Feldman | 600/309 |
| 2005/0215872 A1 | 9/2005 | Berner | 600/347 |
| 2005/0215923 A1 | 9/2005 | Wiegel | 600/573 |
| 2005/0215925 A1 | 9/2005 | Chan | 600/583 |
| 2005/0216046 A1 | 9/2005 | Yeoh | 606/181 |
| 2005/0218024 A1 | 10/2005 | Lang | 206/438 |
| 2005/0221276 A1 | 10/2005 | Rozakis | 435/4 |
| 2005/0221470 A1 | 10/2005 | Matsumoto | 435/287.1 |
| 2005/0222599 A1 | 10/2005 | Czernecki | 606/182 |
| 2005/0227372 A1 | 10/2005 | Khan | 436/514 |
| 2005/0228242 A1 | 10/2005 | Kawamura | 600/300 |
| 2005/0228883 A1 | 10/2005 | Brown | 709/224 |
| 2005/0230252 A1 | 10/2005 | Tsai | 204/450 |
| 2005/0230253 A1 | 10/2005 | Marquant | 204/451 |
| 2005/0232813 A1 | 10/2005 | Karmali | 422/58 |
| 2005/0232815 A1 | 10/2005 | Ruhl | 422/66 |
| 2005/0234368 A1 | 10/2005 | Wong | 600/583 |
| 2005/0234486 A1 | 10/2005 | Allen | 606/181 |
| 2005/0234487 A1 | 10/2005 | Shi | 600/181 |
| 2005/0234488 A1 | 10/2005 | Allen | 606/181 |
| 2005/0234489 A1 | 10/2005 | Allen | 606/181 |
| 2005/0234490 A1 | 10/2005 | Allen | 606/181 |
| 2005/0234491 A1 | 10/2005 | Allen | 606/181 |
| 2005/0234492 A1 | 10/2005 | Tsai | 606/181 |
| 2005/0234494 A1 | 10/2005 | Conway | 606/181 |
| 2005/0234495 A1 | 10/2005 | Schraga | 606/181 |
| 2005/0235060 A1 | 10/2005 | Brown | 709/224 |
| 2005/0239154 A1 | 10/2005 | Feldman | 435/14 |
| 2005/0239156 A1 | 10/2005 | Drucker | 435/14 |
| 2005/0239194 A1 | 10/2005 | Takahashi | 435/287.2 |
| 2005/0240090 A1 | 10/2005 | Ruchti | 600/316 |
| 2005/0240119 A1 | 10/2005 | Draudt | 600/583 |
| 2005/0240207 A1 | 10/2005 | Marshall | 606/181 |
| 2005/0240778 A1 | 10/2005 | Saito | 713/186 |
| 2005/0245798 A1 | 11/2005 | Yamaguchi | 600/345 |
| 2005/0245843 A1 | 11/2005 | Day | 600/583 |
| 2005/0245844 A1 | 11/2005 | Mace | 600/583 |
| 2005/0245845 A1 | 11/2005 | Roe | 600/583 |
| 2005/0245954 A1 | 11/2005 | Roe | 606/181 |
| 2005/0245955 A1 | 11/2005 | Schraga | 606/181 |
| 2005/0256534 A1 | 11/2005 | Alden | 606/182 |
| 2005/0258035 A1 | 11/2005 | Harding | 204/403.01 |
| 2005/0258036 A1 | 11/2005 | Harding | 204/403.01 |
| 2005/0258050 A1 | 11/2005 | Harding | 205/775 |
| 2005/0265094 A1 | 12/2005 | Harding | 365/203 |
| 2005/0276133 A1 | 12/2005 | Harding | 365/203 |
| 2005/0278945 A1 | 12/2005 | Feldman | 29/830 |
| 2005/0279631 A1 | 12/2005 | Celentano | 204/403.01 |
| 2005/0279647 A1 | 12/2005 | Beaty | 205/792 |
| 2005/0283094 A1 | 12/2005 | Thym | 600/583 |
| 2005/0284110 A1 | 12/2005 | Lang | 53/473 |
| 2005/0284757 A1 | 12/2005 | Allen | 204/400 |
| 2005/0287620 A1 | 12/2005 | Heller | 435/14 |
| 2005/0288637 A1 | 12/2005 | Kuhr | 604/204 |
| 2005/0288698 A1 | 12/2005 | Matsumoto | 606/181 |
| 2005/0288699 A1 | 12/2005 | Schraga | 606/181 |
| 2006/0000549 A1 | 1/2006 | Lang | 156/320 |
| 2006/0003398 A1 | 1/2006 | Heller | 435/14 |
| 2006/0004270 A1 | 1/2006 | Bedard | 600/316 |
| 2006/0004271 A1 | 1/2006 | Peyser | 600/362 |
| 2006/0004272 A1 | 1/2006 | Shah | 600/365 |
| 2006/0006574 A1 | 1/2006 | Lang | 264/165 |
| 2006/0008389 A1 | 1/2006 | Sacherer | 422/102 |
| 2006/0015129 A1 | 1/2006 | Shahrokni | 606/181 |
| 2006/0016698 A1 | 1/2006 | Lee | 205/777.5 |
| 2006/0020228 A1 | 1/2006 | Fowler | 600/583 |
| 2006/0024774 A1 | 2/2006 | Zocchi | 435/14 |
| 2006/0025662 A1 | 2/2006 | Buse | 600/347 |
| 2006/0029979 A1 | 2/2006 | Bai | 435/7.1 |
| 2006/0029991 A1 | 2/2006 | Hagino | 435/14 |
| 2006/0030028 A1 | 2/2006 | Nakaminami | 435/287.2 |
| 2006/0030030 A1 | 2/2006 | Wong | 600/583 |
| 2006/0034728 A1 | 2/2006 | Kloepfer | 422/68.1 |
| 2006/0040333 A1 | 2/2006 | Zocchi | 435/14 |
| 2006/0047220 A1 | 3/2006 | Sakata | 600/583 |
| 2006/0047294 A1 | 3/2006 | Mori | 606/181 |
| 2006/0052723 A1 | 3/2006 | Roe | 600/583 |
| 2006/0052724 A1 | 3/2006 | Roe | 600/583 |
| 2006/0052809 A1 | 3/2006 | Karbowniczek | 606/181 |
| 2006/0052810 A1 | 3/2006 | Freeman | 606/181 |
| 2006/0058827 A1 | 3/2006 | Sakata | 606/181 |
| 2006/0058828 A1 | 3/2006 | Shi | 606/181 |
| 2006/0062852 A1 | 3/2006 | Holmes | 424/484 |
| 2006/0063988 A1 | 3/2006 | Schurman | 600/316 |
| 2006/0064035 A1 | 3/2006 | Wang | 600/583 |
| 2006/0079739 A1 | 4/2006 | Wang | 600/300 |
| 2006/0079810 A1 | 4/2006 | Patel | 600/583 |
| 2006/0079811 A1 | 4/2006 | Roe | 600/583 |
| 2006/0079920 A1 | 4/2006 | Schraga | 606/181 |
| 2006/0081469 A1 | 4/2006 | Lee | 204/403.02 |
| 2006/0085020 A1 | 4/2006 | Freeman | 606/181 |
| 2006/0085137 A1 | 4/2006 | Bartkowiak | 702/19 |
| 2006/0086624 A1 | 4/2006 | Tapsak | 205/775 |
| 2006/0088945 A1 | 4/2006 | Douglas | 436/518 |
| 2006/0089566 A1 | 4/2006 | DeHart | 600/573 |
| 2006/0091006 A1 | 5/2006 | Wang | 204/403.02 |
| 2006/0094944 A1 | 5/2006 | Chuang | 600/347 |
| 2006/0094947 A1 | 5/2006 | Kovatchev | 600/365 |
| 2006/0094986 A1 | 5/2006 | Neel | 600/583 |
| 2006/0095061 A1 | 5/2006 | Trautman | 606/185 |
| 2006/0096859 A1 | 5/2006 | King Tong Lau | 204/403.14 |
| 2006/0099107 A1 | 5/2006 | Yamamoto | 422/57 |
| 2006/0099703 A1 | 5/2006 | Choi | 435/287.1 |
| 2006/0100542 A9 | 5/2006 | Wong | 600/583 |
| 2006/0100543 A1 | 5/2006 | Raney | 600/583 |
| 2006/0100654 A1 | 5/2006 | Fukuda | 606/181 |
| 2006/0100655 A1 | 5/2006 | Leong | 606/181 |
| 2006/0100656 A1 | 5/2006 | Olsen | 606/181 |

| Publication No. | Date | Name | Class |
|---|---|---|---|
| 2006/0106373 A1 | 5/2006 | Cahir | 606/9 |
| 2006/0108236 A1 | 5/2006 | Kasielke | 205/792 |
| 2006/0113187 A1 | 6/2006 | Deng | 204/403.01 |
| 2006/0115857 A1 | 6/2006 | Keen | 435/7.1 |
| 2006/0116562 A1 | 6/2006 | Acosta | 600/316 |
| 2006/0116704 A1 | 6/2006 | Ashby | 606/167 |
| 2006/0116705 A1 | 6/2006 | Schraga | 606/181 |
| 2006/0119362 A1 | 6/2006 | Kermani | 324/324 |
| 2006/0121547 A1 | 6/2006 | McIntire | 435/14 |
| 2006/0121625 A1 | 6/2006 | Clemens | 436/514 |
| 2006/0121759 A1 | 6/2006 | Kasai | 439/188 |
| 2006/0122099 A1 | 6/2006 | Aoki | 514/3 |
| 2006/0122536 A1 | 6/2006 | Haar | 600/581 |
| 2006/0129065 A1 | 6/2006 | Matsumoto | 600/583 |
| 2006/0129172 A1 | 6/2006 | Crossman | 606/181 |
| 2006/0129173 A1 | 6/2006 | Wilkinson | 606/181 |
| 2006/0134713 A1 | 6/2006 | Rylatt | 435/7.92 |
| 2006/0140457 A1 | 6/2006 | Simshauser | 382/124 |
| 2006/0144704 A1 | 7/2006 | Ghesquiere | 204/403.01 |
| 2006/0151323 A1 | 7/2006 | Cho | 204/403.04 |
| 2006/0151342 A1 | 7/2006 | Yaguchi | 206/306 |
| 2006/0155215 A1 | 7/2006 | Cha | 600/583 |
| 2006/0155316 A1 | 7/2006 | Perez | 606/181 |
| 2006/0155317 A1 | 7/2006 | List | 606/181 |
| 2006/0156796 A1 | 7/2006 | Burke | 73/61.44 |
| 2006/0157362 A1 | 7/2006 | Schraga | 206/363 |
| 2006/0161078 A1 | 7/2006 | Schraga | 600/583 |
| 2006/0161194 A1 | 7/2006 | Freeman | 606/185 |
| 2006/0166302 A1 | 7/2006 | Clarke | 435/25 |
| 2006/0167382 A1 | 7/2006 | Deshmukh | 600/583 |
| 2006/0169599 A1 | 8/2006 | Feldman | 205/792 |
| 2006/0173254 A1 | 8/2006 | Acosta | 600/316 |
| 2006/0173255 A1 | 8/2006 | Acosta | 600/316 |
| 2006/0173379 A1 | 8/2006 | Rasch-Menges | 600/583 |
| 2006/0173380 A1 | 8/2006 | Hoenes | 600/583 |
| 2006/0173478 A1 | 8/2006 | Schraga | 606/181 |
| 2006/0175216 A1 | 8/2006 | Freeman | 206/363 |
| 2006/0178573 A1 | 8/2006 | Kermani | 600/347 |
| 2006/0178599 A1 | 8/2006 | Faupel | 600/578 |
| 2006/0178600 A1 | 8/2006 | Kennedy | 600/584 |
| 2006/0178686 A1 | 8/2006 | Schraga | 606/181 |
| 2006/0178687 A1 | 8/2006 | Freeman | 606/181 |
| 2006/0178688 A1 | 8/2006 | Freeman | 606/181 |
| 2006/0178689 A1 | 8/2006 | Freeman | 606/181 |
| 2006/0178690 A1 | 8/2006 | Freeman | 606/181 |
| 2006/0183871 A1 | 8/2006 | Ward | 525/464 |
| 2006/0183983 A1 | 8/2006 | Acosta | 600/316 |
| 2006/0184101 A1 | 8/2006 | Srinivasan | 604/68 |
| 2006/0188395 A1 | 8/2006 | Taniike | 422/57 |
| 2006/0189895 A1 | 8/2006 | Neel | 600/584 |
| 2006/0191787 A1 | 8/2006 | Wang | 204/400 |
| 2006/0195023 A1 | 8/2006 | Acosta | 600/316 |
| 2006/0195047 A1 | 8/2006 | Freeman | 600/583 |
| 2006/0195128 A1 | 8/2006 | Alden | 606/181 |
| 2006/0195129 A1 | 8/2006 | Freeman | 606/181 |
| 2006/0195130 A1 | 8/2006 | Freeman | 606/181 |
| 2006/0195131 A1 | 8/2006 | Freeman | 606/181 |
| 2006/0195132 A1 | 8/2006 | Freeman | 606/181 |
| 2006/0195133 A1 | 8/2006 | Freeman | 606/181 |
| 2006/0196031 A1 | 9/2006 | Hoenes | 29/432 |
| 2006/0196795 A1 | 9/2006 | Windus-Smith | 206/438 |
| 2006/0200044 A1 | 9/2006 | Freeman | 600/583 |
| 2006/0200045 A1 | 9/2006 | Roe | 600/583 |
| 2006/0200046 A1 | 9/2006 | Windus-Smith | 600/583 |
| 2006/0200181 A1 | 9/2006 | Fukuzawa | 606/181 |
| 2006/0200981 A1 | 9/2006 | Bhullar | 29/847 |
| 2006/0200982 A1 | 9/2006 | Bhullar | 29/847 |
| 2006/0204399 A1 | 9/2006 | Freeman | 422/58 |
| 2006/0205029 A1 | 9/2006 | Heller | 435/25 |
| 2006/0205060 A1 | 9/2006 | Kim | 435/287.2 |
| 2006/0206135 A1 | 9/2006 | Uehata | 606/181 |
| 2006/0211127 A1 | 9/2006 | Iwaki | 436/169 |
| 2006/0211927 A1 | 9/2006 | Acosta | 600/316 |
| 2006/0211931 A1 | 9/2006 | Blank | 600/344 |
| 2006/0219551 A1 | 10/2006 | Edelbrock | 204/403.14 |
| 2006/0222567 A1 | 10/2006 | Kloepfer | 422/68.1 |
| 2006/0224171 A1 | 10/2006 | Sakata | 606/181 |
| 2006/0224172 A1 | 10/2006 | LeVaughn | 606/181 |
| 2006/0229532 A1 | 10/2006 | Wong | 600/583 |
| 2006/0229533 A1 | 10/2006 | Hoenes | 600/584 |
| 2006/0229651 A1 | 10/2006 | Marshall | 606/181 |
| 2006/0231396 A1 | 10/2006 | Yamaoka | 204/403.14 |
| 2006/0231418 A1 | 10/2006 | Harding | 205/775 |
| 2006/0231442 A1 | 10/2006 | Windus-Smith | 206/438 |
| 2006/0234369 A1 | 10/2006 | Sih | 435/287.1 |
| 2006/0235284 A1 | 10/2006 | Lee | 600/345 |
| 2006/0235454 A1 | 10/2006 | LeVaughn | 606/181 |
| 2006/0241517 A1 | 10/2006 | Fowler | 600/583 |
| 2006/0241666 A1 | 10/2006 | Briggs | 606/181 |
| 2006/0241667 A1 | 10/2006 | Freeman | 606/181 |
| 2006/0241668 A1 | 10/2006 | Schraga | 606/181 |
| 2006/0241669 A1 | 10/2006 | Stout | 606/182 |
| 2006/0247554 A1 | 11/2006 | Roe | 600/583 |
| 2006/0247555 A1 | 11/2006 | Harttig | 600/584 |
| 2006/0247670 A1 | 11/2006 | LeVaughn | 606/181 |
| 2006/0247671 A1 | 11/2006 | Levaughn | 606/182 |
| 2006/0259057 A1 | 11/2006 | Kim | 606/181 |
| 2006/0259058 A1 | 11/2006 | Schiff | 606/181 |
| 2006/0259060 A1 | 11/2006 | Whitson | 606/182 |
| 2006/0264718 A1 | 11/2006 | Ruchti | 600/310 |
| 2006/0264996 A1 | 11/2006 | Levaughn | 606/181 |
| 2006/0264997 A1 | 11/2006 | Colonna | 606/181 |
| 2006/0271083 A1 | 11/2006 | Boecker | 606/181 |
| 2006/0271084 A1 | 11/2006 | Schraga | 606/182 |
| 2006/0276724 A1 | 12/2006 | Freeman | 600/583 |
| 2006/0277048 A1 | 12/2006 | Kintzig | 704/275 |
| 2006/0278545 A1 | 12/2006 | Henning | 206/363 |
| 2006/0282109 A1 | 12/2006 | Jansen | 606/181 |
| 2006/0286620 A1 | 12/2006 | Werner | 435/14 |
| 2006/0287664 A1 | 12/2006 | Grage | 606/181 |
| 2006/0293577 A1 | 12/2006 | Morrison | 600/365 |
| 2007/0004989 A1 | 1/2007 | Dhillon | 600/583 |
| 2007/0004990 A1 | 1/2007 | Kistner | 600/583 |
| 2007/0007183 A1 | 1/2007 | Schulat | 209/573 |
| 2007/0009381 A1 | 1/2007 | Schulat | 422/58 |
| 2007/0010839 A1 | 1/2007 | Galloway | 606/167 |
| 2007/0010841 A1 | 1/2007 | Teo | 606/181 |
| 2007/0015978 A1 | 1/2007 | Kanayama | 600/310 |
| 2007/0016079 A1 | 1/2007 | Freeman | 600/476 |
| 2007/0016103 A1 | 1/2007 | Calasso | 600/583 |
| 2007/0016104 A1 | 1/2007 | Jansen | 600/583 |

FOREIGN PATENT DOCUMENTS

| | | |
|---|---|---|
| DE | 29824204 | 10/2000 |
| DE | 10032042 | 1/2002 |
| DE | 10057832 | 2/2002 |
| DE | 10057832 C1 | 2/2002 |
| DE | 10142232 | 3/2003 |
| DE | 10208575 C1 | 8/2003 |
| DE | 10245721 | 12/2003 |
| DE | 10361560 A1 | 7/2005 |
| EP | 0199484 A2 | 10/1986 |
| EP | 0289 269 | 11/1988 |
| EP | 0320109 | 6/1989 |
| EP | 0 364 208 A1 | 4/1990 |
| EP | 0170375 | 5/1990 |
| EP | 0136362 | 12/1990 |
| EP | 0453283 | 10/1991 |
| EP | 0263948 | 2/1992 |
| EP | 0374355 | 6/1993 |
| EP | 0351891 | 9/1993 |
| EP | 0593096 | 4/1994 |
| EP | 0415388 | 5/1995 |
| EP | 0505494 | 7/1995 |
| EP | 0359831 | 8/1995 |

| | | | | | | |
|---|---|---|---|---|---|---|
| EP | 0471986 | 10/1995 | | WO | WO 97/18464 | 5/1997 |
| EP | 0368474 | 12/1995 | | WO | WO 97/30344 | 8/1997 |
| EP | 0461601 | 12/1995 | | WO | WO 97/42882 | 11/1997 |
| EP | 0429076 | 1/1996 | | WO | WO 97/42888 | 11/1997 |
| EP | 0552223 | 7/1996 | | WO | WO 97/45720 | 12/1997 |
| EP | 0735363 | 10/1996 | | WO | WO 98/03431 | 1/1998 |
| EP | 0505504 | 3/1997 | | WO | WO 98/19159 | 5/1998 |
| EP | 0406304 | 8/1997 | | WO | WO 98/20332 | 5/1998 |
| EP | 0537761 | 8/1997 | | WO | WO 98/20348 | 5/1998 |
| EP | 0795601 | 9/1997 | | WO | WO 98/24366 | 6/1998 |
| EP | 0562370 | 11/1997 | | WO | WO 98/24373 | 6/1998 |
| EP | 0415393 | 12/1997 | | WO | WO 98/35225 | 8/1998 |
| EP | 0560336 | 5/1998 | | WO | WO 99/03584 | 1/1999 |
| EP | 0878 708 | 11/1998 | | WO | WO 99/05966 | 2/1999 |
| EP | 0 898 936 A2 | 3/1999 | | WO | WO 99/07431 A1 | 2/1999 |
| EP | 0505475 | 3/1999 | | WO | WO 99/13100 | 3/1999 |
| EP | 0901018 | 3/1999 | | WO | WO 99/17854 | 4/1999 |
| EP | 0470649 | 6/1999 | | WO | WO 99/18532 | 4/1999 |
| EP | 0 951 939 | 10/1999 | | WO | WO 99/19507 | 4/1999 |
| EP | 0 951 939 A2 | 10/1999 | | WO | WO 99/19717 | 4/1999 |
| EP | 0847447 | 11/1999 | | WO | WO 99/27483 | 6/1999 |
| EP | 0964059 | 12/1999 | | WO | WO 99/27852 | 6/1999 |
| EP | 0969097 | 1/2000 | | WO | WO 99/62576 | 12/1999 |
| EP | 0 985 376 | 5/2000 | | WO | WO 99/64580 | 12/1999 |
| EP | 1021950 | 7/2000 | | WO | WO 00/06024 | 2/2000 |
| EP | 0894869 | 2/2001 | | WO | WO 00/09184 | 2/2000 |
| EP | 1074832 | 2/2001 | | WO | WO 00/11578 | 3/2000 |
| EP | 1093854 | 4/2001 | | WO | WO 00/15103 | 3/2000 |
| EP | 1 101 443 | 5/2001 | | WO | WO 00/17799 | 3/2000 |
| EP | 1101443 | 5/2001 | | WO | WO 00/17800 | 3/2000 |
| EP | 1114995 | 7/2001 | | WO | WO 00/18293 | 4/2000 |
| EP | 0736607 | 8/2001 | | WO | WO 00/19346 | 4/2000 |
| EP | 0874984 | 11/2001 | | WO | WO 00/30186 | 5/2000 |
| EP | 0730037 | 12/2001 | | WO | WO 00/32097 | 6/2000 |
| EP | 0636879 | 1/2002 | | WO | WO 00/32098 | 6/2000 |
| EP | 01174083 | 1/2002 | | WO | WO 00/33236 | 6/2000 |
| EP | 0851224 | 3/2002 | | WO | WO 00/39914 | 7/2000 |
| EP | 0759553 | 5/2002 | | WO | WO 00/42422 | 7/2000 |
| EP | 0856586 | 5/2002 | | WO | WO 00/44084 | 7/2000 |
| EP | 0817809 | 7/2002 | | WO | WO 00/50771 | 8/2000 |
| EP | 0872728 | 7/2002 | | WO | WO 00/60340 | 10/2000 |
| EP | 0795748 | 8/2002 | | WO | WO 00/64022 | 10/2000 |
| EP | 0685737 | 9/2002 | | WO | WO 00/67245 | 11/2000 |
| EP | 0958495 | 11/2002 | | WO | WO 00/67268 | 11/2000 |
| EP | 0937249 | 12/2002 | | WO | WO 00/72452 | 11/2000 |
| EP | 0880692 | 1/2004 | | WO | WO 01/00090 | 1/2001 |
| EP | 01374770 | 1/2004 | | WO | WO 01/00090 A1 | 1/2001 |
| EP | 1246688 | 5/2004 | | WO | 01/16578 A1 | 3/2001 |
| EP | 1502614 | 2/2005 | | WO | WO 01/75433 | 3/2001 |
| EP | 1101443 | * 9/2005 ................ 606/181 | WO | WO 01/23885 | 4/2001 |
| FR | 2 555 432 A | 5/1985 | | WO | WO 01/25775 | 4/2001 |
| GB | 2168815 | 6/1986 | | WO | WO 01/26813 | 4/2001 |
| GB | 233936 A | 6/1999 | | WO | WO 01/33216 | 5/2001 |
| GB | 2335860 A | 10/1999 | | WO | WO 01/34029 | 5/2001 |
| GB | 2335990 A | 10/1999 | | WO | WO 01/36955 | 5/2001 |
| JP | 2-326247 | 11/1990 | | WO | WO 01/37174 | 5/2001 |
| JP | 10-296325 | 10/1998 | | WO | 01/45014 A1 | 6/2001 |
| WO | WO 80/01389 | 7/1980 | | WO | WO 01/40788 | 7/2001 |
| WO | WO 85/04089 | 9/1985 | | WO | WO 01/57510 | 8/2001 |
| WO | WO 86/07632 | 12/1986 | | WO | WO 01/64105 | 9/2001 |
| WO | WO 91/09139 | 6/1991 | | WO | WO 01/66010 | 9/2001 |
| WO | WO 93/06979 | 4/1993 | | WO | WO 01/66010 A1 | 9/2001 |
| WO | WO 93/25898 | 12/1993 | | WO | WO 01/69505 | 9/2001 |
| WO | WO 94/27140 | 11/1994 | | WO | WO 01/72220 A | 10/2001 |
| WO | WO 94/29703 | 12/1994 | | WO | WO 01/72225 | 10/2001 |
| WO | WO 94/29704 | 12/1994 | | WO | WO 01/73124 | 10/2001 |
| WO | WO 94/29731 | 12/1994 | | WO | WO 01/73395 | 10/2001 |
| WO | WO 95/00662 | 1/1995 | | WO | WO 01/89691 | 11/2001 |
| WO | WO 95/10223 | 4/1995 | | WO | WO 02/00101 | 1/2002 |
| WO | WO 95/22597 | 8/1995 | | WO | WO 02/02796 | 1/2002 |
| WO | WO 96/30431 | 10/1996 | | WO | WO 02/08750 | 1/2002 |
| WO | WO 97/02359 | 1/1997 | | WO | WO 02/08753 | 1/2002 |
| WO | WO 97/02487 | 1/1997 | | WO | WO 02/08950 | 1/2002 |

| | | |
|---|---|---|
| WO | WO 02/18940 | 3/2002 |
| WO | WO 02/21317 | 3/2002 |
| WO | WO 02/25551 | 3/2002 |
| WO | WO 02/32559 | 4/2002 |
| WO | WO 02/41227 | 5/2002 |
| WO | WO 02/41779 | 5/2002 |
| WO | WO 02/44948 | 6/2002 |
| WO | WO 02/056769 A1 | 7/2002 |
| WO | WO 02/059734 | 8/2002 |
| WO | WO 02/069791 | 9/2002 |
| WO | WO 02/077638 | 10/2002 |
| WO | WO 02/100251 | 12/2002 |
| WO | WO 02/100252 | 12/2002 |
| WO | WO 02/100253 | 12/2002 |
| WO | WO 02/100254 | 12/2002 |
| WO | WO 02/100460 | 12/2002 |
| WO | WO 02/100461 | 12/2002 |
| WO | WO 02/101343 | 12/2002 |
| WO | WO 02/101359 | 12/2002 |
| WO | WO 03/000321 | 1/2003 |
| WO | WO 03/023389 | 3/2003 |
| WO | WO 03/042691 | 5/2003 |
| WO | WO 03/045557 | 6/2003 |
| WO | WO 03/046542 | 6/2003 |
| WO | WO 03/049609 | 6/2003 |
| WO | WO 03/050534 | 6/2003 |
| WO | WO 03/066128 | 8/2003 |
| WO | WO 03/070099 | 8/2003 |
| WO | WO 03/071940 | 9/2003 |
| WO | WO 03/088851 A1 | 10/2003 |
| WO | WO 03/094752 | 11/2003 |
| WO | WO 03/101297 | 12/2003 |
| WO | WO 2004/008130 | 1/2004 |
| WO | WO 2004/022133 | 3/2004 |
| WO | WO 2004/026130 | 4/2004 |
| WO | WO 2004/040285 A2 | 5/2004 |
| WO | WO 2004/040287 A1 | 5/2004 |
| WO | WO 2004/040948 | 5/2004 |
| WO | WO 2004/041082 | 5/2004 |
| WO | WO 2004/054455 | 7/2004 |
| WO | WO 2004/060174 | 7/2004 |
| WO | WO 2004/060446 | 7/2004 |
| WO | WO 2004/091693 | 10/2004 |
| WO | WO 2004/098405 | 11/2004 |
| WO | WO 2004/003147 | 12/2004 |
| WO | WO 2004/107964 | 12/2004 |
| WO | WO 2004/107975 | 12/2004 |
| WO | WO 2004/112602 | 12/2004 |
| WO | WO 2005/001418 | 1/2005 |
| WO | WO 2005/006939 | 1/2005 |
| WO | WO 2005/011774 | 2/2005 |
| WO | WO 2005/016125 | 2/2005 |
| WO | WO 2005/018425 | 3/2005 |
| WO | WO 2005/018430 | 3/2005 |
| WO | WO 2005/018454 | 3/2005 |
| WO | WO 2005/018709 | 3/2005 |
| WO | WO 2005/018710 | 3/2005 |
| WO | WO 2005/018711 | 3/2005 |
| WO | WO 2005/022143 | 3/2005 |
| WO | WO 2005/023088 | 3/2005 |
| WO | WO 2005/033659 | 4/2005 |
| WO | WO 2005/034720 | 4/2005 |
| WO | WO 2005/034721 | 4/2005 |
| WO | WO 2005/034741 | 4/2005 |
| WO | WO 2005/034778 | 4/2005 |
| WO | WO 2005/035017 | 4/2005 |
| WO | WO 2005/035018 | 4/2005 |
| WO | WO 2005/037095 | 4/2005 |
| WO | WO 2005/046477 | 5/2005 |
| WO | WO 2005/065399 | 7/2005 |
| WO | WO 2005/065414 | 7/2005 |
| WO | WO 2005/065415 | 7/2005 |
| WO | WO 2006005545 A2 | 7/2005 |
| WO | WO 2005/072604 | 8/2005 |
| WO | WO 2005/084557 | 9/2005 |
| WO | WO 2005/116622 | 12/2005 |
| WO | WO 2005/119234 | 12/2005 |
| WO | WO 2005/121759 | 12/2005 |
| WO | WO 2006/001973 | 1/2006 |
| WO | WO 2006/011062 | 2/2006 |
| WO | WO 2006/013045 | 2/2006 |
| WO | WO 2006/027702 A2 | 3/2006 |
| WO | WO 2006/032391 | 3/2006 |
| WO | WO 2006/072004 | 7/2006 |

OTHER PUBLICATIONS

International Search Report (PCT/ISA/220) for PCT/US02/19058.
International Search Report (PCT/ISA/220) for PCT/US02/19054.
International Search Report (PCT/ISA/220) for PCT/US02/19059.
Written Opinion (certain documents cited) for PCT/US02/19059.
International Search Report (PCT/ISA/220) for PCT/US02/19060.
International Search Report (PCT/ISA/220) for PCT/US02/19450.
International Search Report (PCT/ISA/220) for PCT/US02/19057.
International Search Report (PCT/ISA/220) for PCT/US02/19053.
International Search Report (PCT/ISA/220) for PCT/US02/19188.
International Search Report (PCT/ISA/220) for PCT/US03/12555.
International Search Report (PCT/ISA/220) for PCT/US03/12381.
International Search Report (PCT/ISA/220) for PCT/US03/12546.
International search Report (PCT/ISA/220) for PCT/US03/35015.
International Search Report (PCT/ISA/220) for PCT/US03/40095.
International Search Report (PCT/ISA/220) for PCT/US03/41747.

* cited by examiner

METHOD AND APPARATUS FOR IMPROVING SUCCESS RATE OF BLOOD YIELD FROM A FINGERSTICK

TECHNICAL FIELD

Lancing devices are well known in the medical health-care products industry for piercing the skin to produce blood for analysis. Biochemical analysis of blood samples is a diagnostic tool for determining clinical information. Many point-of-care tests are performed using capillary whole blood, the most common being monitoring diabetic blood glucose level. Other uses for this method include the analysis of oxygen and coagulation based on Prothrombin time measurement. Typically, a drop of blood for this type of analysis is obtained by making a small incision in the fingertip, creating a small wound which generates a small blood droplet on the surface of the skin.

BACKGROUND ART

Early methods of lancing included piercing or slicing the skin with a needle or razor. Current methods utilize lancing devices that contain a multitude of spring, cam and mass actuators to drive the lancet. These include cantilever springs, diaphragms, coil springs, as well as gravity plumbs used to drive the lancet. Typically, the device is pre-cocked or the user cocks the device. The device is held against the skin and mechanically triggers the ballistic launch of the lancet. The forward movement and depth of skin penetration of the lancet is determined by a mechanical stop and/or dampening, as well as a spring or cam which retract the lancet.

Variations in skin thickness and hydration can yield different results from different users of the lancing device. Current devices rely on adjustable mechanical stops or damping to control the lancet's depth of penetration and compensate for skin thickness and hydration. Such mechanical stops do not regulate the acceleration in order to control the velocity of the lancet as it is protracted and retracted. Conversely, cams offer rough control of lancet velocity in and out of the skin, but do not allow for compensation for skin thickness and hydration. Hence, not-all lancing events are successful in generating a blood sample sufficient for the desired analytical test.

Success rate means the probability of producing a blood sample with one lancing action which is sufficient in volume to perform the desired analytical test. The blood droplet produced by the action must reach the surface of the skin to be viable for testing. In some instances, blood will flow from the cut blood vessels but is trapped below the surface of the skin, forming a hematoma. In other instances, a subcutaneous wound is created, but no external blood is obtained. The success rate of obtaining an acceptable blood sample with industry standard lancets available on the market today is 75% to 80%; meaning that up to one in five lancing operations will yield insufficient blood or no blood. For patients required to self test five to six times daily, this inability to obtain a blood droplet every time the finger is lanced translates into needlessly repeating a painful protocol.

DISCLOSURE OF INVENTION

In accordance with some embodiments of the invention, a method for lancing uses a lancet, a helix, or an elastomer to maintain the patency of the wound tract once the lancet has cut into the skin. If penetration takes place, and an appropriate number of blood vessels are cut, blood is allowed to flow up through the wound tract and onto the surface of the skin because the lancet, the helix, or the elastomer coats or braces the wound tract, keeping it open and patent. Coating or bracing is defined generally as keeping the wound open so that the blood from the capillaries can reach the surface of the finger. The term flow control can include any means for bracing the wound tract created by the lancet.

It is to be understood that both the foregoing general description and the following detailed description are exemplary and explanatory only and are not restrictive of the invention, as claimed.

BRIEF DESCRIPTION OF DRAWING

The objects, advantages and features of this invention will be more readily appreciated from the following detailed description, when read in conjunction with the accompanying drawing, in which.

BEST MODE FOR CARRYING OUT THE INVENTION

Figure 1:
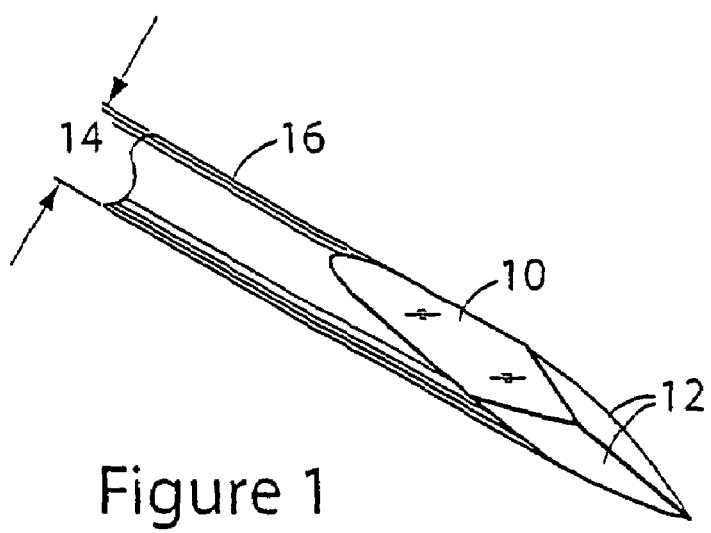
FIG. 1 illustrates a typical lancet showing the parameters which affect lancing pain, blood volume, and success rate.

FIG. 1 shows a standard industry lancet for glucose testing which has a three-facet geometry. The lancet (16) is produced by taking a rod of diameter (14) and grinding a plane 8 degrees to the plane of the primary axis to create the primary facet (10). The secondary facets (12) are then created by rotating the shaft of the needle 15 degrees, and then rolling over 12 degrees to the plane of the primary facet. Other possible geometries require altering the lancet's production parameters such as shaft diameter, angles, and translation distance.

Figure 2:
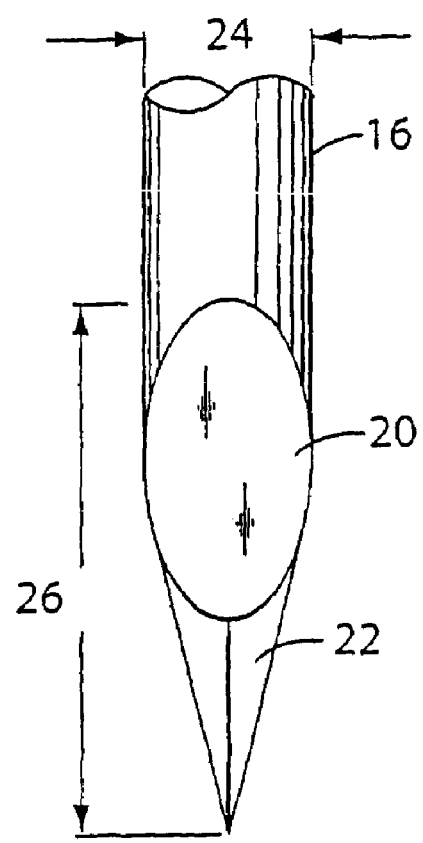
FIG. 2 illustrates lancet parameters.

FIG. 2 illustrates facet and tip geometry (20) and (22), diameter (24), and depth (26) which are significant factors in reducing pain, blood volume and success rate. It is known that additional cutting by the lancet is achieved by increasing the shear percentage or ratio of the primary to secondary facets, which when combined with reducing the lancet's diameter reduces skin tear and penetration force and gives the perception of less pain. Overall success rate of blood yield, however, also depends on a variety of factors, including the existence of facets, facet geometry, and skin anatomy.

Anatomically, the fingertip has a capillary mesh network sufficient to yield 30 to 60 microliters of blood, but the fingertip also has a dense nerve network. The thenar web's nerve network is less dense than the fingertip, but the thenar web also has a less dense capillary network which cannot offer blood volume on the order of the fingertip. The forearm does not produce successful blood samples due to the completely different skin tensile properties. The wound tract seals up following lancet withdrawal, preventing the blood from reaching the surface, and lancing is usually accompanied by hematoma. Lancing the forearm requires large diameter lancets and active pumping to collect enough blood for testing.

Other known mechanisms for increasing the success rate of blood yield rely on creating a vacuum, suctioning the wound, applying an adhesive strip, vibration while cutting, or initiating a second lance if the first is unsuccessful. None of these methods address the interaction of the lancet with the tissue during wound creation.

Reference will now be made in detail to embodiments of the devices and methods having features of the invention. Lancing is defined generally herein as penetrating the skin and cutting blood vessels for the purpose of collecting a blood sample. In some embodiments of the invention, lancet interaction with the skin tissue is controlled while creating the wound so as to yield an appropriate amount of blood every time. Achieving a sampling success rate to near 100% can be an important factor to successfully combining sampling and acquisition of the sample into an integrated sampling module. An example of an integrated sampling module could be an integrated glucose sampling module which incorporates a glucose test strip.

Slowed retraction of a lancet embodiment braces the wound by keeping the tract from closing and keeping the flap created at the skin surface from sealing the opening at the top of the tract. During the slowed retraction, blood is allowed to accumulate and follow the lancet back through the incision. Embodiments of the present invention contemplate numerous devices and methods for providing such blood flow control. To achieve a controlled slowed retraction, a lancet driver is preferably able to retract the lancet at a different velocity than the velocity of the lancet during creation of the incision. Such controlled retraction is achieved by altering spring or cam drivers, or using an electric lancet actuator so that retraction velocity follows a predetermined profile.

Figure 3:
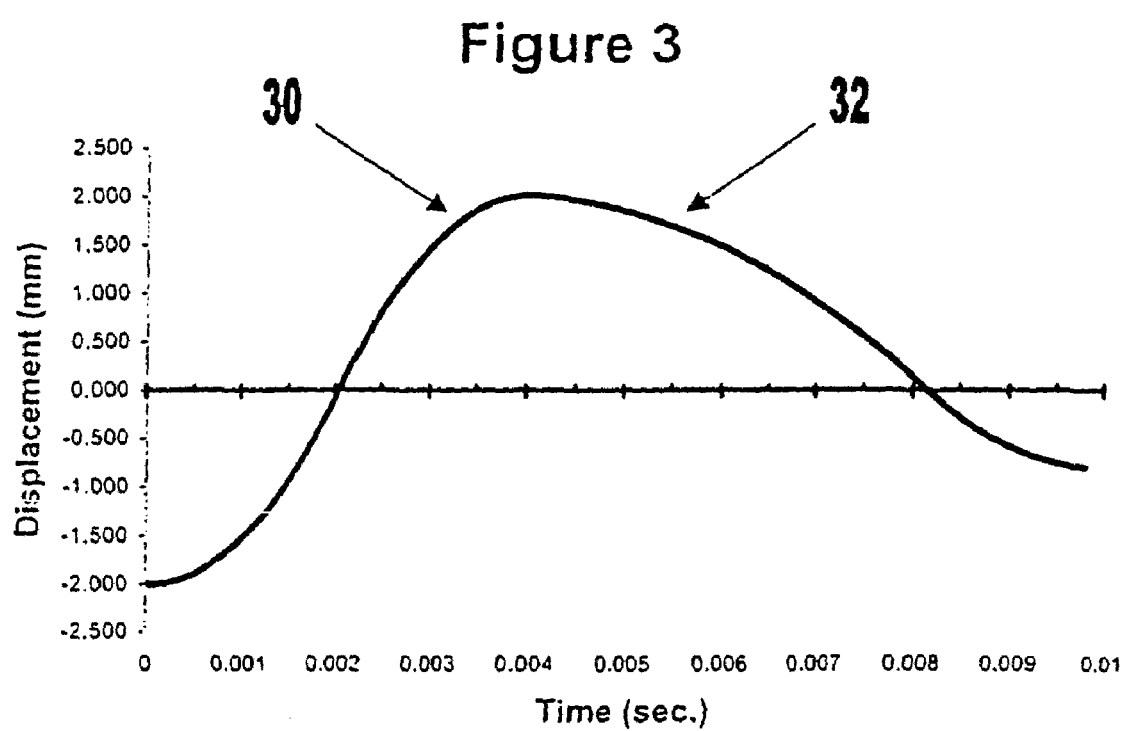
FIG. 3 is a graph showing displacement of the lancet over time.
Figure 4:
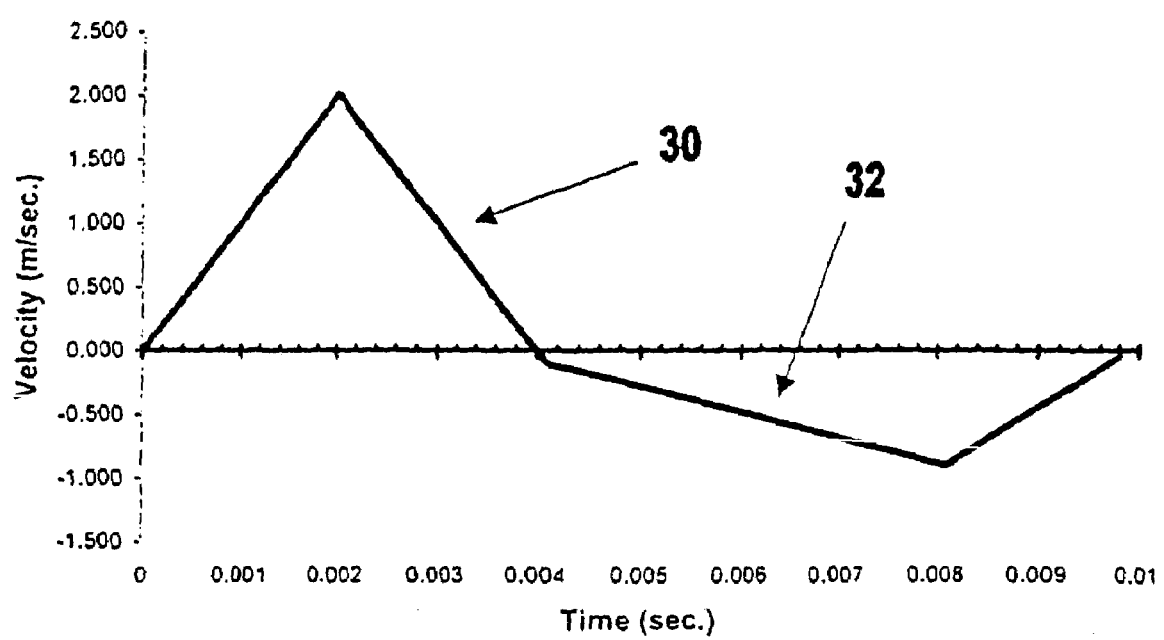
FIG. 4 is a graph showing velocity of the lancet over time for slowed retraction of the lancet embodiment.

FIG. 3 shows the displacement versus time profile of a lancet for a controlled lancet retraction for one embodiment. FIG. 4 shows the velocity of the lancet versus time profile of the lancet for a controlled retraction. The lancet driving mechanism controls lancet displacement and velocity at several steps in the lancing cycle, including when the lancet cuts the blood vessels to allow blood to pool (30), and as the lancet retracts, regulating the retraction rate to allow the blood to flood the wound tract while keeping the wound flap from sealing the channel (32) to permit blood to exit the wound. This can be achieved by a mechanical or electric actuator. An electric actuator is described in U.S. Pat. No. 7,025,774, Inventors: Don Alden, et al., entitled "ELECTRIC LANCET ACTUATOR") submitted on the same day and assigned to the same assignee as the present application. This application discloses a mechanism for driving a lancet, to achieve the controlled retraction described in the present invention. Said application is incorporated by reference in its entirety herein. A processor is provided that modulates the power from a power supply to a lancet driver through an amplifier. The processor measures the location of a lancet using a position sensing mechanism through an analog to digital converter. The processor calculates the movement of the lancet by comparing the actual profile of the lancet to the predetermined profile. The processor modulates the power to the lancet driver 68 through a signal generator, which controls the amplifier so that the actual profile of the lancet does not exceed the predetermined profile by more than a preset error limit. The error limit is the accuracy in the control of the lancet.

Control during retraction of the lancet involves controlling the velocity of the lancet based on the lancet position. This can be done using a mechanically predetermined path or can be dynamically altered using an electrical position feedback mechanism as described in a copending application (PCT/US02/19053, Inventors: Dominique Freeman, et al., entitled "SELF-OPTIMIZING LANCING DEVICE WITH ADAPTATION MEANS TO TEMPORAL VARIATIONS IN CUTANEOUS PROPERTIES") submitted on the same day and assigned to the same assignee as the present application. This copending application discloses embodiments that that control a lancet to achieve a controlled retraction. Said copending application is incorporated by reference in its entirety herein.

Figure 5:
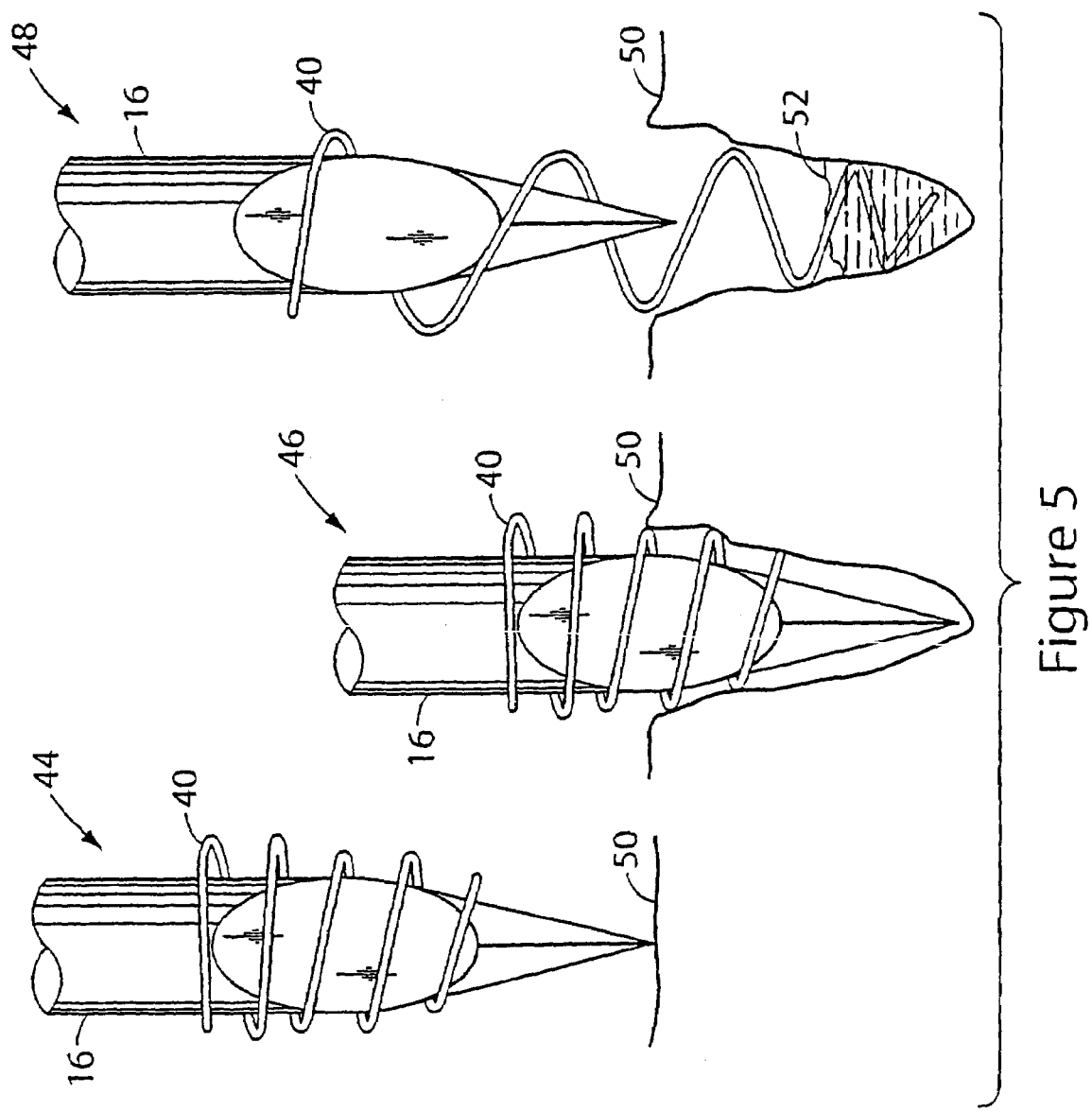
FIG. 5 illustrates the lancet before, during and after the incision for a retractable coil embodiment.

FIG. 5 shows the use of an embodiment of the invention which includes a retractable coil. A coiled helix or tube (40) is attached externally to lancet (42) with the freedom to slide such that when the lancet penetrates the skin (50), the helix or tube (40) follows the trajectory of the lancet (16). The helix begins the lancing cycle coiled around the facets and shaft of the lancet (44). As the lancet penetrates the skin, the helix braces the wound tract around the lancet (46). As the lancet retracts, the helix remains to brace open the wound tract, keeping the wound tract from collapsing and keeping the surface skin flap from closing (48). This allows blood (52) to pool and flow up the channel to the surface of the skin. The helix is then retracted as the lancet pulls the helix to the point where the helix is decompressed to the point where the diameter of the helix becomes less than the diameter of the wound tract and becomes dislodged from the skin.

The tube or helix (40) is made of wire or metal of the type commonly used in angioplasty stents such as stainless steel, nickel titanium allow or the like. Alternatively the tube or helix (40) or a ring can be made of a biodegradable material, which braces the wound tract by becoming lodged in the skin. Biodegradation is completed within seconds or minutes of insertion, allowing adequate time for blood to pool and flow up the wound tract. Biodegradation is activated by heat or pH from the skin.

Other methods of keeping the wound open include coating the lancet with a powder, which coats the wound tract and keeps it open when the lancet is withdrawn. The powder is a coarse bed of microspheres or capsules which hold the channel open while allowing blood to flow through the porous interstices.

In another embodiment the wound is held open using a two part needle, the outer part in the shape of a "U" and the inner part filling the "U." After creating the wound the inner needle is withdrawn leaving an open channel, rather like the plugs that are commonly used for withdrawing sap from maple trees.

Figure 6:
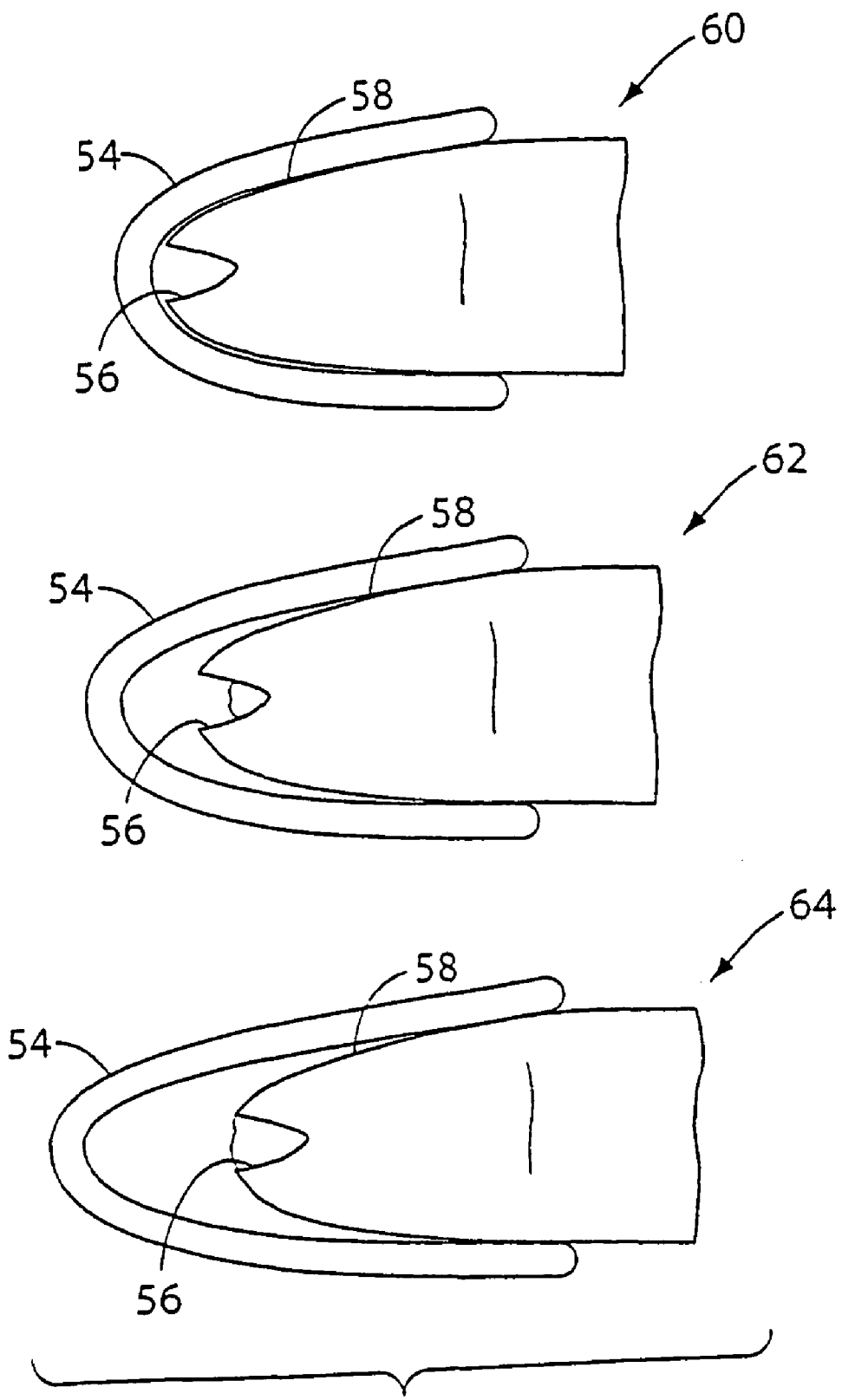
FIG. 6 illustrates a finger wound tract braced in the elastomer embodiment.

FIG. 6 shows a further embodiment of this invention utilizing an elastomer to, coat the wound. This method uses an elastomer (54), such as silicon rubber, to coat or brace the wound tract (56) by covering and stretching the surface of the finger (58). The elastomer (54) is applied to the finger (58) prior to lancing. After a short delay, the lancet (not shown) then penetrates the elastomer (54) and the skin on the surface of the finger (58) as is seen in (60). Blood is allowed to pool and rise to the surface while the elastomer (54) braces the wound tract (56) as is seen in (62) and (64). An added benefit of using the elastomer (54) to cover the skin is seamless sampling for blood gas analysis as described in U.S. Pat. No. 7,001,344, Inventors: Vladimir Drbal, et al., entitled "BLOOD SAMPLING DEVICE WITH DIAPHRAGM ACTUATED LANCET") submitted on the same day and assigned to the same assignee as the present application. This application discloses how to acquire a blood sample that is not contaminated by substantial amounts of ambient air, and could therefore provide a viable sample of gas analysis. Said application is incorporated by reference in its entirety herein.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method for sampling blood comprising the steps of:
using an electronic driver to drive a penetrating member and lance a piece of skin to create an incision and a wound tract, the electronic driver being coupled to a processor and the processor being coupled to an amplifier; and
using the amplifier to modulate power from a power supply to the electronic driver to provide a controlled slowed retraction of the penetrating member at a different velocity than a velocity of the penetrating member during creation of the incision, the slowed retraction of the penetrating member creating a bracing of the wound by keeping the tract from closing and keeping a flap created at a skin surface from sealing an opening at a top of the tract, wherein control during retraction of the penetrating member includes controlling velocity of the penetrating member based on penetrating member position using a mechanically predetermined path or an electrical position feedback mechanism.

2. A method of sampling blood according to claim 1 wherein:
said bracing comprises controlling the retraction velocity of a lancet.

3. A method for sampling blood according to claim 2 wherein:
said controlling comprises of monitoring the displacement of the lancet.

4. A method of sampling blood according to claim 1 wherein:
said bracing comprises inserting a tube in the wound tract.

5. A method of sampling blood according to claim 1 wherein:
said bracing comprises stretching the piece of skin before and after said lancing.

6. A method of sampling blood comprising the steps of:
puncturing a piece of skin to create a wound tract; and
bracing said wound tract with a biodegradable structure to provide a controlled slowed retraction of the penetrating member at a different velocity than a velocity of the penetrating member during creation of the incision and permit a controlled sample of blood to exit said wound tract, the slowed retraction of the penetrating member creating a bracing of the wound by keeping the tract from closing and keeping a flap created at a skin surface from sealing an opening at a top of the tract, wherein control during retraction of the penetrating member includes controlling velocity of the penetrating member based on penetrating member position using a mechanically predetermined path or an electrical position feedback mechanism.

* * * * *

UNITED STATES PATENT AND TRADEMARK OFFICE
CERTIFICATE OF CORRECTION

| | | |
|---|---|---|
| PATENT NO. | : 7,699,791 B2 | Page 1 of 1 |
| APPLICATION NO. | : 10/363509 | |
| DATED | : April 20, 2010 | |
| INVENTOR(S) | : Alden et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 829 days.

Signed and Sealed this
Eleventh Day of January, 2011

David J. Kappos
*Director of the United States Patent and Trademark Office*